United States Patent [19]
Bandman et al.

[11] Patent Number: 5,932,475
[45] Date of Patent: Aug. 3, 1999

[54] HUMAN NUCLEOLIN-LIKE PROTEIN

[75] Inventors: Olga Bandman, Mountain View; Henry Yue, Sunnyvale; Neil C. Corley, Mountain View; Purvi Shah, Sunnyvale, all of Calif.

[73] Assignee: Incyte Pharmaceuticals, Inc., Palo Alto, Calif.

[21] Appl. No.: 08/990,114

[22] Filed: Dec. 12, 1997

[51] Int. Cl.⁶ .................................................. C12N 15/00
[52] U.S. Cl. ..................... 435/320.1; 530/350; 536/23.1; 536/23.5; 435/69.1; 435/6
[58] Field of Search .......................... 530/350; 536/23.1, 536/23.5; 435/320.1, 69.1, 6

[56] References Cited

PUBLICATIONS

Lapeyre, B. et al., "Nucleolin, the major nucleolar protein of growing eukaryotic cells: An unusual protein structure revealed by the nucleotide sequence", *Proc. Natl. Acad. Sci. USA*, 84: 1472–1476 (1987).

Erard, M.S. et al., "A major nucleolar protein, nucleolin, induces chromatin decondensation by binding to histone H1", *Eur. J. Biochem.*, 175: 525–530 (1988).

Deng, J.S. et al., "Internalization of anti–nucleolin antibody into viable HEp–2 cells", *Mol. Biol. Rep.*, 23: 191–195 (1996).

Bell, S.A. et al., "Specificity of antinuclear antibodies in scleroderma–like chronic graft–versus–host disease: clinical correlation and histocompatibility locus antigen association", *Br. J. Dermatol.*, 134: 848–854 (1996).

Zaidi, S.H.E. and J.S. Malter, "Nucleolin and Heterogeneous Nuclear Ribonucleoprotein C Proteins Specifically Interact with the 3'–Untranslated Region of Amyloid Protein Precursor mRNA", *J. Biol. Chem.*, 270: 17292–17298 (1995).

Lapeyre, B. et al., (Direct Submission), GenBank Sequence Database (Accession 128842), National Center for Biotechnology Information, National Library of Medicine, Bethesda, Maryland, 20894, (GI 128842).

*Primary Examiner*—Sheela Huff
*Attorney, Agent, or Firm*—Incyte Pharmaceuticals, Inc.

[57] ABSTRACT

The invention provides a human nucleolin-like protein (HNLP) and polynucleotides which identify and encode HNLP. The invention also provides expression vectors, host cells, antibodies, agonists, and antagonists. The invention also provides methods for treating or preventing disorders associated with expression of HNLP.

10 Claims, 9 Drawing Sheets

```
                   10              19              28              37              46              55
5' G GGC GCG CGC    GCG CAC CGG    GAG CGC GCT    CGG AGG CGA    GTG GAA CTG    GAT CGG GTT 64              73              82              91             100             109
   TGC TGC CAG    CGG CGT GAG    CTT CGG CCG    GCA TTT CGG    TAC AAC AGC    TCC ACT CGC GCC 118             127             136             145             154             163
   GGA CAC AGG    GAG CAG CGA    GCA CGC CGG    CTT TCC CGC    AAC CCA ATA    CCA TCG GAC AGG 172             181             190             199             208             217
   ATT TCT CCG    CCT CAG CCC    AAC GGG GAG    ATC TCT GGA    AAC ATG GCT    ACA GAA CAT
                                                                    M   A     T   E   H 226             235             244             253             262             271
   GTT AAT GGA    AAT ACT GAA    GAG CCC ATG    GAT ACT ACT    TCT GCA GTT    ATC CAT
   V   N   G      N   T   E      E   P   M      D   T   T      S   A   V      I   H 280             289             298             307             316             325
   TCA GAA AAT    TTT CAG ACA    TTG CTT GAT    GCT GGT TTA    CCA CAG AAA    GTT GCT GAA
   S   E   N      F   Q   T      L   L   D      A   G   L      P   Q   K      V   A   E 334             343             352             361             370             379
   AAA CTA GAT    GAA ATT TAC    GTT GCA GGG    CTA GTT GCA    CAT AGT GAT    TTA GAT GAA
   K   L   D      E   I   Y      V   A   G      L   V   A      H   S   D      L   D   E
```

FIGURE 1A

```
                388       397       406       415       424       433
AGA GCT ATT GAA GCT TTA AAA GAA TTC AAT GAA GAC GGT GCA TTG GCA GTT CTT
 R   A   I   E   A   L   K   E   F   N   E   D   G   A   L   A   V   L 442       451       460       469       478       487
CAA CAG TTT AAA GAC AGT GAT CTC TCT CAT GTT CAG AAC AAA AGT GCC TTT TTA
 Q   Q   F   K   D   S   D   L   S   H   V   Q   N   K   S   A   F   L 496       505       514       523       532       541
TGT GGA GTC ATG AAG ACT TAC AGG AGA GAA CAG AGA GAA CAA GGG ACC AAA GTA GCA
 C   G   V   M   K   T   Y   R   R   E   Q   R   E   K   Q   G   T   K   V   A 550       559       568       577       586       595
GAT TCT AGT AAA GGA CCA GAT GAG GCA AAA ATT AAG GCA CTC TTG GAA AGA ACA
 D   S   S   K   G   P   D   E   A   K   I   K   A   L   L   E   R   T 604       613       622       631       640       649
GGC TAC ACA CTT GAT GTG ACC ACT GGA CAG AGG AAG TAT GGA GGA CCA CCT CCA
 G   Y   T   L   D   V   T   T   G   Q   R   K   Y   G   G   P   P   P 658       667       676       685       694       703
GAT TCC GTT TAT TCA GGT CAG CAG CCT TCT GTT GGC ACT GAG ATA TTT GTG GGA
 D   S   V   Y   S   G   Q   Q   P   S   V   G   T   E   I   F   V   G
```

FIGURE 1B

|     | 712 |     | 721 |     | 730 |     | 739 |     | 748 |     | 757 |
|-----|-----|-----|-----|-----|-----|-----|-----|-----|-----|-----|-----|
| AAG | ATC | CCA | AGA | GAT | CTA | TTT | GAG | GAT | GAA | CTT | GTT | CCA | TTA | TTT | GAG | AAA | GCT |
| K   | I   | P   | R   | D   | L   | F   | E   | D   | E   | L   | V   | P   | L   | F   | E   | K   | A   |

|     | 766 |     | 775 |     | 784 |     | 793 |     | 802 |     | 811 |
| GGA | CCT | ATA | TGG | GAT | CTT | CGT | CTA | ATG | ATG | GAT | CCA | CTC | ACT | GGT | CTC | AAT | AGA |
| G   | P   | I   | W   | D   | L   | R   | L   | M   | M   | D   | P   | L   | T   | G   | L   | N   | R   |

|     | 820 |     | 829 |     | 838 |     | 847 |     | 856 |     | 865 |
| GGT | TAT | GCG | TTT | GTC | ACT | TTT | TGT | ACA | AAA | GAA | GCA | GCT | CAG | GAG | GCT | GTT | AAA |
| G   | Y   | A   | F   | V   | T   | F   | C   | T   | K   | E   | A   | A   | Q   | E   | A   | V   | K   |

|     | 874 |     | 883 |     | 892 |     | 901 |     | 910 |     | 919 |
| CTG | TAT | AAT | AAT | CAT | GAA | ATT | CGT | TCT | GGA | AAA | CAT | ATT | GGT | GTC | TGC | ATC | TCA |
| L   | Y   | N   | N   | H   | E   | I   | R   | S   | G   | K   | H   | I   | G   | V   | C   | I   | S   |

|     | 928 |     | 937 |     | 946 |     | 955 |     | 964 |     | 973 |
| GTT | GCC | AAC | AAT | AGG | CTT | TTT | GTG | GGC | TCT | ATT | CCT | AAG | AGT | AAA | ACC | AAG | GAA |
| V   | A   | N   | N   | R   | L   | F   | V   | G   | S   | I   | P   | K   | S   | K   | T   | K   | E   |

|     | 982 |     | 991 |     | 1000 |     | 1009 |     | 1018 |     | 1027 |
| CAG | ATT | CTT | GAA | GAA | TTT | AGC | AAA | GTA | ACA | GAG | GGT | CTT | ACA | GAC | GTC | ATT | TTA |
| Q   | I   | L   | E   | E   | F   | S   | K   | V   | T   | E   | G   | L   | T   | D   | V   | I   | L   |

FIGURE 1C

```
      1036            1045          1054           1063          1072           1081
TAC CAC CAA CCG GAT GAC AAG AAA AAC AGA GGC TTT TGC TTT CTT GAA TAT
 Y   H   Q   P   D   D   K   K   N   R   G   F   C   F   L   E   Y 1090            1099          1108           1117          1126           1135
GAA GAT CAC AAA ACA GCT GCC CAG AGG CGT AGG TTA ATG AGT GGT AAA GTC
 E   D   H   K   T   A   A   Q   R   R   R   L   M   S   G   K   V 1144            1153          1162           1171          1180           1189
AAG GTC TGG GGG AAT GTT GGA ACT GTT GAA TGG GCT GAT CCT ATA GAA GAT CCT
 K   V   W   G   N   V   G   T   V   E   W   A   D   P   I   E   D   P 1198            1207          1216           1225          1234           1243
GAT CCT GAG GTT ATG GCA AAG GTA AAG GTG CTG TTT GTA CGC AAC CTT GCC AAT
 D   P   E   V   M   A   K   V   K   V   L   F   V   R   N   L   A   N 1252            1261          1270           1279          1288           1297
ACT GTA ACA GAA GAG ATT TTA GAA AAG GCA TTT AGT CAG TTT GGG AAA CTG GAA
 T   V   T   E   E   I   L   E   K   A   F   S   Q   F   G   K   L   E 1306            1315          1324           1333          1342           1351
CGA GTG AAG AAG TTA AAA GAT TAT GCG TTC ATT CAT TTT GAT GAG CGA GAT GGT
 R   V   K   K   L   K   D   Y   A   F   I   H   F   D   E   R   D   G
```

FIGURE 1D

```
      1360               1369          1378          1387          1396          1405
GCT GTC AAG GCT ATG GAA GAA ATG AAT GGC AAA GAC TTG GAG GGA GAA AAT ATT
 A   V   K   A   M   E   E   M   N   G   K   D   L   E   G   E   N   I 1414               1423          1432          1441          1450          1459
GAA ATT GTT TTT GCC AAG CCA CCA GAT CAG AAA AGG AAA GAA AGA AAA GCT CAG
 E   I   V   F   A   K   P   P   D   Q   K   R   K   E   R   K   A   Q 1468               1477          1486          1495          1504          1513
AGG CAA GCA GCA AAA AAT CAA ATG TAT GAC TAC TAC TAT GGT CCA CCT
 R   Q   A   A   K   N   Q   M   Y   D   Y   Y   Y   G   P   P 1522               1531          1540          1549          1558          1567
CAT ATG CCC CCT CCA ACA AGA GGT CGA GGG CGT GGA GGT AGA GGT TAT GGA
 H   M   P   P   P   T   R   G   R   G   R   G   G   R   G   Y   G 1576               1585          1594          1603          1612          1621
TAT CCT CCA GAT TAT TAT GGA TAT GAA GAT TAT TAT GAT TAT TAT GGT TAT GAT
 Y   P   P   D   Y   Y   G   Y   E   D   Y   Y   D   Y   Y   G   Y   D 1630               1639          1648          1657          1666          1675
TAC CAT AAC TAT CGT GGT GGA TAT GAA GAT CCA TAC TAT GGT TAT GAA GAT TTT
 Y   H   N   Y   R   G   G   Y   E   D   P   Y   Y   G   Y   E   D   F
```

FIGURE 1E

```
      1684           1693           1702           1711           1720           1729
CAA GTT GGA GCT AGA GGA AGG GGT AGA GGA GCA AGG GGT GCT GCT CCA TCC
 Q   V   G   A   R   G   R   G   R   G   A   R   G   A   A   P   S 1738           1747           1756           1765           1774           1783
AGA GGT CGT GGG GCT CCT CCC CGC GGT AGA GCC GGT TAT TCA CAG AGA GGA
 R   G   R   G   A   P   P   R   G   R   A   G   Y   S   Q   R   G 1792           1801           1810           1819           1828           1837
GGT CCT GGA TCA GCA AGA GGC GTT CGA GCA GGG AAA AGG GGT CGA GGC CGG TCC
 G   P   G   S   A   R   G   V   R   A   G   K   R   G   R   G   R   S 1846           1855           1864           1873           1882           1891
TGA CCT GTT ACA ATG AAG ACT GAC TTG CTA TGT GGG ATT ACA CCA GAA GCT TGC 1900           1909           1918           1927           1936           1945
AGT GGA GTA ATG GTA AGG AAA TCA AGC AAC CTT AAA TAT GTC GGC TGT ATA GGA 1954           1963           1972           1981           1990           1999
GCA TAT TCT ATT GCA GAA GAC CTT CCT ATG AAG ATC ATG GAA TCA AAT ACG GGA 2008           2017           2026           2035           2044           2053
CAT TGA ACT AAT ACT TGG ACT TTG ATA TGA ATT TCT TTA ACA ATT TTC TCT GCA 2062           2071
GTG CAA GTT ATT AAA CTA CTA AAG CTA CT 3'
```

FIGURE 1F

```
1    MA-  -TEHVNGNGTEEPMDTTSAVIHSENFQ           2809795
1    MVKLAKAGKTHGEAKKMAPPPKEVEEDSED             GI 128842

29   TL L-  - - - - - - - - - - - - DAGLPQKVAEKLDE- - -  2809795
31   EEMSEEDDSSGEEVVIPQKKGKKATATPA              GI 128842

46   - - IYVA-  - - - - - - - - - - - - - - - - - - - -  2809795
61   KKVVVSQTKKVAVPTPAKKAAVTPGKKAAA             GI 128842

50   - - - - - - - - - - - - - - - - - - GLVA-  - - - -  2809795
91   TPAKKAVTPAKAVATPGKGATQAKALVAT              GI 128842

54   - - - - - - - - - - - - - - - - HSDLDERA-  - - - -  2809795
121  PGKKGAVTPAKGAKNGKNAKKEDSDEDD               GI 128842

62   IEALKEFNEDGALAVLQQFKDSDLSHVQNK             2809795
151  DDDEDDSDEDEEEDEFEPPVVKGKQGK                GI 128842

92   SAFLCGVMKTYRQREKQGTKVADSSKGPDE             2809795
181  VAAAPASEDEDEEEDEEEEDDS                     GI 128842

122  AKIKALL-  - - - - - - - - - - - ERT-                2809795
211  EEEEAMEITPAKGKKAPAKVPVKAKNVAEEE            GI 128842

129  - - - - - - - - - - - - - - - - - - - - - - - - -  2809795
241  EDDDEEDEEEDEEEDEDEEEDDDEE                  GI 128842
```

HUMAN NUCLEOLIN-LIKE PROTEIN

FIELD OF THE INVENTION

This invention relates to nucleic acid and amino acid sequences of a human nucleolin-like protein and to the use of these sequences in the diagnosis, treatment, and prevention of cancer, autoimmune disorders, and Alzheimer's disease.

BACKGROUND OF THE INVENTION

The nuclei of eukaryotic cells contain a subcompartment termed the nucleolus, which is the site of ribosome production. Ribosomes are comprised of ribosomal RNA and various protein components imported from the cytoplasm. Ribosomes are essential scaffolding and catalytic elements of the protein translation machinery found in the cytosol.

The main protein component in the nucleolus of eukaryotic cells is nucleolin. Nucleolin is an essential component of ribosome biogenesis. The carboxy-terminus of nucleolin is a glycine-rich region that contains RNA binding domains, which interact specifically with stem-loop structures typical of ribosomal RNA. The amino-terminus of nucleolin contains a binding site for histone H1, and binding of nucleolin to H1 promotes the decondensation of chromatin necessary to begin DNA transcription. Nucleolin also contains binding sites for nuclear localization sequences, and has been shown to shuttle between the nucleus and the cytoplasm. Thus, nucleolin also plays a role in importing proteins into the nucleus, and is a crucial element of ribosome biogenesis. (Lapeyre, B. et al. (1987) Proc. Natl. Acad. Sci.84:1472–1476; Erard, M. S. et al. (1988) Eur. J. Biochem. 175:525–530.)

Elevated levels of autoantibodies to nucleolin are implicated in autoimmune diseases such as systemic sclerosis, systemic lupus erythematosus, and certain cases of chronic graft-versus-host disease. (Deng, J. S. et al. (1996) Mol. Biol. Rep. 23:191–195) In addition, there is a clinical correlation between disease severity and levels of autoantibodies to nucleolin. (Bell, S. A. et al. (1996) Br. J. Dermatol. 134:848–854.) Thus, overexpression of nucleolin and the mislocalization of nucleolin outside the nucleolus may mediate various autoimmune disorders.

One characteristic of Alzheimer's disease is the deposition of senile, or neuritic, plaques throughout the brains of affected individuals. These senile plaques contain βA4 amyloid protein, which is produced from β amyloid precursor protein (APP). Messenger RNA for APP is elevated in the brains of Alzheimer's disease patients, and nucleolin has been shown to bind and stabilize APP mRNA, increasing the message's half-life and thereby increasing the level of APP. Thus, nucleolin regulates APP expression, and therefore is involved in overproduction of βA4 amyloid protein and the deposition of senile plaques in Alzheimer's disease. (Zaidi, S. H. E. and Malter, J. S. (1995) J Biol Chem 270:17292–17298.)

The discovery of a new human nucleolin-like protein and the polynucleotides encoding it satisfies a need in the art by providing new compositions which are useful in the diagnosis, treatment, and prevention of cancer, autoimmune disorders, and Alzheimer's disease.

SUMMARY OF THE INVENTION

The invention features a substantially purified polypeptide, human nucleolin-like protein (HNLP), comprising the amino acid sequence of SEQ ID NO:1 or a fragment of SEQ ID NO:1.

The invention further provides a substantially purified variant of HNLP having at least 90% amino acid identity to the amino acid sequence of SEQ ID NO:1 or a fragment of SEQ ID NO:1. The invention also provides an isolated and purified polynucleotide sequence encoding the polypeptide comprising the amino acid sequence of SEQ ID NO:1 or a fragment of SEQ ID NO:1. The invention also includes an isolated and purified polynucleotide variant having at least 90% polynucleotide identity to the polynucleotide sequence encoding the polypeptide comprising the amino acid sequence of SEQ ID NO:1 or a fragment of SEQ ID NO:1.

Additionally, the invention provides a composition comprising a polynucleotide sequence encoding the polypeptide comprising the amino acid sequence of SEQ ID NO:1 or a fragment of SEQ ID NO:1. The invention further provides an isolated and purified polynucleotide sequence which hybridizes under stringent conditions to the polynucleotide sequence encoding the polypeptide comprising the amino acid sequence of SEQ ID NO:1 or a fragment of SEQ ID NO:1, as well as an isolated and purified polynucleotide sequence which is complementary to the polynucleotide sequence encoding the polypeptide comprising the amino acid sequence of SEQ ID NO:1 or a fragment of SEQ ID NO:1.

The invention also provides an isolated and purified polynucleotide sequence comprising SEQ ID NO:2 or a fragment of SEQ ID NO:2, and an isolated and purified polynucleotide variant having at least 90% polynucleotide identity to the polynucleotide sequence comprising SEQ ID NO:2 or a fragment of SEQ ID NO:2. The invention also provides an isolated and purified polynucleotide sequence which is complementary to the polynucleotide sequence comprising SEQ ID NO:2 or a fragment of SEQ ID NO:2.

The invention further provides an expression vector containing at least a fragment of the polynucleotide sequence encoding the polypeptide comprising the amino acid sequence of SEQ ID NO:1 or a fragment of SEQ ID NO:1. In another aspect, the expression vector is contained within a host cell.

The invention also provides a method for producing a polypeptide comprising the amino acid sequence of SEQ ID NO:1 or a fragment of SEQ ID NO:1, the method comprising the steps of: (a) culturing the host cell containing an expression vector containing at least a fragment of a polynucleotide sequence encoding HNLP under conditions suitable for the expression of the polypeptide; and (b) recovering the polypeptide from the host cell culture.

The invention also provides a pharmaceutical composition comprising a substantially purified HNLP having the amino acid sequence of SEQ ID NO:1 or a fragment of SEQ ID NO:1 in conjunction with a suitable pharmaceutical carrier.

The invention further includes a purified antibody which binds to a polypeptide comprising the amino acid sequence of SEQ ID NO:1 or a fragment of SEQ ID NO:1, as well as a purified agonist and a purified antagonist of the polypeptide.

The invention also provides a method for treating or preventing a cancer, the method comprising administering to a subject in need of such treatment an effective amount of an antagonist of HNLP.

The invention also provides a method for treating or preventing an autoimmune disorder, the method comprising administering to a subject in need of such treatment an effective amount of an antagonist of HNLP.

The invention also provides a method for treating or preventing Alzheimer's disease, the method comprising administering to a subject in need of such treatment an effective amount of an antagonist of HNLP.

The invention also provides a method for detecting a polynucleotide encoding HNLP in a biological sample containing nucleic acids, the method comprising the steps of: (a) hybridizing the complement of the polynucleotide sequence encoding the polypeptide comprising SEQ ID NO:1 or a fragment of SEQ ID NO:1 to at least one of the nucleic acids of the biological sample, thereby forming a hybridization complex; and (b) detecting the hybridization complex, wherein the presence of the hybridization complex correlates with the presence of a polynucleotide encoding HNLP in the biological sample. In one aspect, the nucleic acids of the biological sample are amplified by the polymerase chain reaction prior to the hybridizing step.

BRIEF DESCRIPTION OF THE FIGURES

FIGS. 1A, 1B, 1C, 1D, 1E, and 1F show the amino acid sequence (SEQ ID NO:1) and nucleic acid sequence (SEQ ID NO:2) of HNLP. The alignment was produced using MACDNASIS PRO™ software (Hitachi Software Engineering Co. Ltd., San Bruno, Calif.).

FIGS. 2A, 2B, and 2C show the amino acid sequence alignments between HNLP (2809795; SEQ ID NO:1), and nucleolin from hamster (GI 128842; SEQ ID NO:3), produced using the multisequence alignment program of DNASTAR™ software (DNASTAR Inc, Madison, Wis.).

DESCRIPTION OF THE INVENTION

Before the present proteins, nucleotide sequences, and methods are described, it is understood that this invention is not limited to the particular methodology, protocols, cell lines, vectors, and reagents described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a," "an," and "the" include plural reference unless the context clearly dictates otherwise. Thus, for example, a reference to "a host cell" includes a plurality of such host cells, and a reference to "an antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are cited for the purpose of describing and disclosing the cell lines, vectors, and methodologies which are reported in the publications and which might be used in connection with the invention. Nothing herein is to be construed as an admission that the invention is not entitled to antedate such disclosure by virtue of prior invention.

DEFINITIONS

"HNLP," as used herein, refers to the amino acid sequences of substantially purified HNLP obtained from any species, particularly a mammalian species, including bovine, ovine, porcine, murine, equine, and preferably the human species, from any source, whether natural, synthetic, semi-synthetic, or recombinant.

The term "agonist," as used herein, refers to a molecule which, when bound to HNLP, increases or prolongs the duration of the effect of HNLP. Agonists may include proteins, nucleic acids, carbohydrates, or any other molecules which bind to and modulate the effect of HNLP.

An "allele" or an "allelic sequence," as these terms are used herein, is an alternative form of the gene encoding HNLP. Alleles may result from at least one mutation in the nucleic acid sequence and may result in altered mRNAs or in polypeptides whose structure or function may or may not be altered. Any given natural or recombinant gene may have none, one, or many allelic forms. Common mutational changes which give rise to alleles are generally ascribed to natural deletions, additions, or substitutions of nucleotides. Each of these types of changes may occur alone, or in combination with the others, one or more times in a given sequence.

"Altered" nucleic acid sequences encoding HNLP, as described herein, include those sequences with deletions, insertions, or substitutions of different nucleotides, resulting in a polynucleotide the same HNLP or a polypeptide with at least one functional characteristic of HNLP. Included within this definition are polymorphisms which may or may not be readily detectable using a particular oligonucleotide probe of the polynucleotide encoding HNLP, and improper or unexpected hybridization to alleles, with a locus other than the normal chromosomal locus for the polynucleotide sequence encoding HNLP. The encoded protein may also be "altered," and may contain deletions, insertions, or substitutions of amino acid residues which produce a silent change and result in a functionally equivalent HNLP. Deliberate amino acid substitutions may be made on the basis of similarity in polarity, charge, solubility, hydrophobicity, hydrophilicity, and/or the amphipathic nature of the residues, as long as the biological or immunological activity of HNLP is retained. For example, negatively charged amino acids may include aspartic acid and glutamic acid, positively charged amino acids may include lysine and arginine, and amino acids with uncharged polar head groups having similar hydrophilicity values may include leucine, isoleucine, and valine; glycine and alanine; asparagine and glutamine; serine and threonine; and phenylalanine and tyrosine.

The terms "amino acid" or "amino acid sequence," as used herein, refer to an oligopeptide, peptide, polypeptide, or protein sequence, or a fragment of any of these, and to naturally occurring or synthetic molecules. In this context, "fragments", "immunogenic fragments", or "antigenic fragments" refer to fragments of HNLP which are preferably about 5 to about 15 amino acids in length and which retain some biological activity or immunological activity of HNLP. Where "amino acid sequence" is recited herein to refer to an amino acid sequence of a naturally occurring protein molecule, "amino acid sequence" and like terms are not meant to limit the amino acid sequence to the complete native amino acid sequence associated with the recited protein molecule.

"Amplification," as used herein, relates to the production of additional copies of a nucleic acid sequence. Amplification is generally carried out using polymerase chain reaction (PCR) technologies well known in the art. (See, e.g., Dieffenbach, C. W. and G. S. Dveksler (1995) *PCR Primer, a Laboratory Manual*, pp.1–5, Cold Spring Harbor Press, Plainview, N.Y.)

The term "antagonist," as it is used herein, refers to a molecule which, when bound to HNLP, decreases the amount or the duration of the effect of the biological or immunological activity of HNLP. Antagonists may include proteins, nucleic acids, carbohydrates, antibodies, or any other molecules which decrease the effect of HNLP.

As used herein, the term "antibody" refers to intact molecules as well as to fragments thereof, such as Fab, F(ab')$_2$, and Fv fragments, which are capable of binding the epitopic determinant. Antibodies that bind HNLP polypeptides can be prepared using intact polypeptides or using fragments containing small peptides of interest as the immunizing antigen. The polypeptide or oligopeptide used to immunize an animal (e.g., a mouse, a rat, or a rabbit) can be derived from the translation of RNA, or synthesized chemically, and can be conjugated to a carrier protein if desired. Commonly used carriers that are chemically coupled to peptides include bovine serum albumin, thyroglobulin, and keyhole limpet hemocyanin (KLH). The coupled peptide is then used to immunize the animal.

The term "antigenic determinant," as used herein, refers to that fragment of a molecule (i.e., an epitope) that makes contact with a particular antibody. When a protein or a fragment of a protein is used to immunize a host animal, numerous regions of the protein may induce the production of antibodies which bind specifically to antigenic determinants (given regions or three-dimensional structures on the protein). An antigenic determinant may compete with the intact antigen (i.e., the immunogen used to elicit the immune response) for binding to an antibody.

The term "antisense," as used herein, refers to any composition containing a nucleic acid sequence which is complementary to a specific nucleic acid sequence. The term "antisense strand" is used in reference to a nucleic acid strand that is complementary to the "sense" strand. Antisense molecules may be produced by any method including synthesis or transcription. Once introduced into a cell, the complementary nucleotides combine with natural sequences produced by the cell to form duplexes and to block either transcription or translation. The designation "negative" can refer to the antisense strand, and the designation "positive" can refer to the sense strand.

As used herein, the term "biologically active," refers to a protein having structural, regulatory, or biochemical functions of a naturally occurring molecule. Likewise, "immunologically active" refers to the capability of the natural, recombinant, or synthetic HNLP, or of any oligopeptide thereof, to induce a specific immune response in appropriate animals or cells and to bind with specific antibodies.

The terms "complementary" or "complementarity," as used herein, refer to the natural binding of polynucleotides under permissive salt and temperature conditions by base pairing. For example, the sequence "A-G-T" binds to the complementary sequence "T-C-A." Complementarity between two single-stranded molecules may be "partial," such that only some of the nucleic acids bind, or it may be "complete," such that total complementarity exists between the single stranded molecules. The degree of complementarity between nucleic acid strands has significant effects on the efficiency and strength of the hybridization between the nucleic acid strands. This is of particular importance in amplification reactions, which depend upon binding between nucleic acids strands, and in the design and use of peptide nucleic acid (PNA) molecules.

A "composition comprising a given polynucleotide sequence" or a "composition comprising a given amino acid sequence," as these terms are used herein, refer broadly to any composition containing the given polynucleotide or amino acid sequence. The composition may comprise a dry formulation, an aqueous solution, or a sterile composition. Compositions comprising polynucleotide sequences encoding HNLP or fragments of HNLP may be employed as hybridization probes. The probes may be stored in freeze-dried form and may be associated with a stabilizing agent such as a carbohydrate. In hybridizations, the probe may be deployed in an aqueous solution containing salts (e.g., NaCl), detergents (e.g., SDS), and other components (e.g., Denhardt's solution, dry milk, salmon sperm DNA, etc.).

The phrase "consensus sequence," as used herein, refers to a nucleic acid sequence which has been resequenced to resolve uncalled bases, extended using the XL-PCR kit (Perkin Elmer, Norwalk, Conn.) in the 5' and/or the 3' direction, and resequenced, or which has been assembled from the overlapping sequences of more than one Incyte Clone using a computer program for fragment assembly, such as the GELVIEW Fragment assembly system (GCG, Madison, Wis.). Some sequences have been both extended and assembled to produce the consensus sequence.

As used herein, the term "correlates with expression of a polynucleotide" indicates that the detection of the presence of nucleic acids, the same or related to a nucleic acid sequence encoding HNLP, by northern analysis is indicative of the presence of nucleic acids encoding HNLP in a sample, and thereby correlates with expression of the transcript from the polynucleotide encoding HNLP.

A "deletion," as the term is used herein, refers to a change in the amino acid or nucleotide sequence that results in the absence of one or more amino acid residues or nucleotides.

The term "derivative," as used herein, refers to the chemical modification of HNLP, of a polynucleotide sequence encoding HNLP, or of a polynucleotide sequence complementary to a polynucleotide sequence encoding HNLP. Chemical modifications of a polynucleotide sequence can include, for example, replacement of hydrogen by an alkyl, acyl, or amino group. A derivative polynucleotide encodes a polypeptide which retains at least one biological or immunological function of the natural molecule. A derivative polypeptide is one modified by glycosylation, pegylation, or any similar process that retains a at least one biological or immunological function of the polypeptide from which it was derived.

The term "homology," as used herein, refers to a degree of complementarity. There may be partial homology or complete homology. The word "identity" may substitute for the word "homology." A partially complementary sequence that at least partially inhibits an identical sequence from hybridizing to a target nucleic acid is referred to as "substantially homologous." The inhibition of hybridization of the completely complementary sequence to the target sequence may be examined using a hybridization assay (Southern or northern blot, solution hybridization, and the like) under conditions of reduced stringency. A substantially homologous sequence or hybridization probe will compete for and inhibit the binding of a completely homologous sequence to the target sequence under conditions of reduced stringency. This is not to say that conditions of reduced stringency are such that non-specific binding is permitted, as reduced stringency conditions require that the binding of two sequences to one another be a specific (i.e., a selective) interaction. The absence of non-specific binding may be tested by the use of a second target sequence which lacks even a partial degree of complementarity (e.g., less than about 30% homology or identity). In the absence of non-specific binding, the substantially homologous sequence or probe will not hybridize to the second non-complementary target sequence.

"Human artificial chromosomes" (HACs), as described herein, are linear microchromosomes which may contain DNA sequences of about 10 kb to 10 Mb in size, and which contain all of the elements required for stable mitotic chromosome segregation and maintenance. (Harrington, J. J. et al. (1997) Nat Genet. 15:345–355.)

The term "humanized antibody," as used herein, refers to antibody molecules in which the amino acid sequence in the non-antigen binding regions has been altered so that the antibody more closely resembles a human antibody, and still retains its original binding ability.

"Hybridization," as the term is used herein, refers to any process by which a strand of nucleic acid binds with a complementary strand through base pairing.

As used herein, the term "hybridization complex" as used herein, refers to a complex formed between two nucleic acid sequences by virtue of the formation of hydrogen bonds between complementary bases. A hybridization complex may be formed in solution (e.g., $C_0t$ or $R_0t$ analysis) or formed between one nucleic acid sequence present in solution and another nucleic acid sequence immobilized on a solid support (e.g., paper, membranes, filters, chips, pins or glass slides, or any other appropriate substrate to which cells or their nucleic acids have been fixed).

The words "insertion" or "addition," as used herein, refer to changes in an amino acid or nucleotide sequence resulting in the addition of one or more amino acid residues or nucleotides, respectively, to the sequence found in the naturally occurring molecule.

The term "microarray," as used herein, refers to an array of distinct polynucleotides or oligonucleotides arrayed on a substrate, such as paper, nylon or any other type of membrane, filter, chip, glass slide, or any other suitable solid support.

The term "modulate," as it appears herein, refers to a change in the activity of HNLP. For example, modulation may cause an increase or a decrease in protein activity, binding characteristics, or any other biological, functional, or immunological properties of HNLP.

The phrases "nucleic acid" or "nucleic acid sequence," as used herein, refer to an oligonucleotide, nucleotide, polynucleotide, or any fragment thereof, to DNA or RNA of genomic or synthetic origin which may be single-stranded or double-stranded and may represent the sense or the antisense strand, to peptide nucleic acid (PNA), or to any DNA-like or RNA-like material. In this context, "fragments" refers to those nucleic acid sequences which are greater than about 60 nucleotides in length, and most preferably are at least about 100 nucleotides, at least about 1000 nucleotides, or at least about 10,000 nucleotides in length.

The term "oligonucleotide," as used herein, refers to a nucleic acid sequence of at least about 6 nucleotides to 60 nucleotides, preferably about 15 to 30 nucleotides, and most preferably about 20 to 25 nucleotides, which can be used in PCR amplification or in a hybridization assay or microarray. As used herein, the term "oligonucleotide" is substantially equivalent to the terms "amplimers," "primers," "oligomers," and "probes," as these terms are commonly defined in the art.

"Peptide nucleic acid" (PNA), as used herein, refers to an antisense molecule or anti-gene agent which comprises an oligonucleotide of at least about 5 nucleotides in length linked to a peptide backbone of amino acid residues ending in lysine. The terminal lysine confers solubility to the composition. PNAs preferentially bind complementary single stranded DNA and RNA and stop transcript elongation, and may be pegylated to extend their lifespan in the cell. (Nielsen, P. E. et al. (1993) Anticancer Drug Des. 8:53–63.).

The term "sample," as used herein, is used in its broadest sense. A biological sample suspected of containing nucleic acids encoding HNLP, or fragments thereof, or HNLP itself may comprise a bodily fluid; an extract from a cell, chromosome, organelle, or membrane isolated from a cell; a cell; genomic DNA, RNA, or cDNA (in solution or bound to a solid support); a tissue; a tissue print; and the like.

As used herein, the terms "specific binding" or "specifically binding" refer to that interaction between a protein or peptide and an agonist, an antibody, or an antagonist. The interaction is dependent upon the presence of a particular structure of the protein recognized by the binding molecule (i.e., the antigenic determinant or epitope). For example, if an antibody is specific for epitope "A," the presence of a polypeptide containing the epitope A, or the presence of free unlabeled A, in a reaction containing free labeled A and the antibody will reduce the amount of labeled A that binds to the antibody.

As used herein, the term "stringent conditions" refers to conditions which permit hybridization between polynucleotide sequences and the claimed polynucleotide sequences. Suitably stringent conditions can be defined by, for example, the concentrations of salt or formamide in the prehybridization and hybridization solutions, or by the hybridization temperature, and are well known in the art. In particular, stringency can be increased by reducing the concentration of salt, increasing the concentration of formamide, or raising the hybridization temperature.

For example, hybridization under high stringency conditions could occur in about 50% formamide at about 37° C. to 42° C. Hybridization could occur under reduced stringency conditions in about 35% to 25% formamide at about 30° C. to 35° C. In particular, hybridization could occur under high stringency conditions at 42° C. in 50% formamide, 5× SSPE, 0.3% SDS, and 200 μg/ml sheared and denatured salmon sperm DNA. Hybridization could occur under reduced stringency conditions as described above, but in 35% formamide at a reduced temperature of 35° C. The temperature range corresponding to a particular level of stringency can be further narrowed by calculating the purine to pyrimidine ratio of the nucleic acid of interest and adjusting the temperature accordingly. Variations on the above ranges and conditions are well known in the art.

The term "substantially purified," as used herein, refers to nucleic acid or amino acid sequences that are removed from their natural environment and are isolated or separated, and are at least about 60% free, preferably about 75% free, and most preferably about 90% free from other components with which they are naturally associated.

A "substitution," as used herein, refers to the replacement of one or more amino acids or nucleotides by different amino acids or nucleotides, respectively.

"Transformation," as defined herein, describes a process by which exogenous DNA enters and changes a recipient cell. Transformation may occur under natural or artificial conditions according to various methods well known in the art, and may rely on any known method for the insertion of foreign nucleic acid sequences into a prokaryotic or eukaryotic host cell. The method for transformation is selected based on the type of host cell being transformed and may include, but is not limited to, viral infection, electroporation, heat shock, lipofection, and particle bombardment. The term "transformed" cells includes stably transformed cells in which the inserted DNA is capable of replication either as an autonomously replicating plasmid or as part of the host chromosome, and refers to cells which transiently express the inserted DNA or RNA for limited periods of time.

A "variant" of HNLP, as used herein, refers to an amino acid sequence that is altered by one or more amino acids. The variant may have "conservative" changes, wherein a substituted amino acid has similar structural or chemical properties (e.g., replacement of leucine with isoleucine). More rarely, a variant may have "nonconservative" changes (e.g., replacement of glycine with tryptophan). Analogous minor variations may also include amino acid deletions or insertions, or both. Guidance in determining which amino acid residues may be substituted, inserted, or deleted without abolishing biological or immunological activity may be found using computer programs well known in the art, for example, DNASTAR software.

THE INVENTION

The invention is based on the discovery of a new human nucleolin-like protein (HNLP), the polynucleotides encoding HNLP, and the use of these compositions for the diagnosis, treatment, or prevention of cancer, autoimmune disorders, and Alzheimer's disease.

Nucleic acids encoding the HNLP of the present invention were first identified in Incyte Clone 2809795 from the lymphocyte cDNA library (TLYMNOT05) using a computer search for amino acid sequence alignments. A consensus sequence, SEQ ID NO:2, was derived from the following overlapping and/or extended nucleic acid sequences: Incyte Clones 2809795 (TLYMNOT05), 3403115 (ESOGNOT03), 1466025 (PANCTUT02), 073781 (THPIPEB01), 002356 (U937NOT01), 2845548 (DRGLNOT01), and 825607 (PROSNOT06).

Figure 2B:
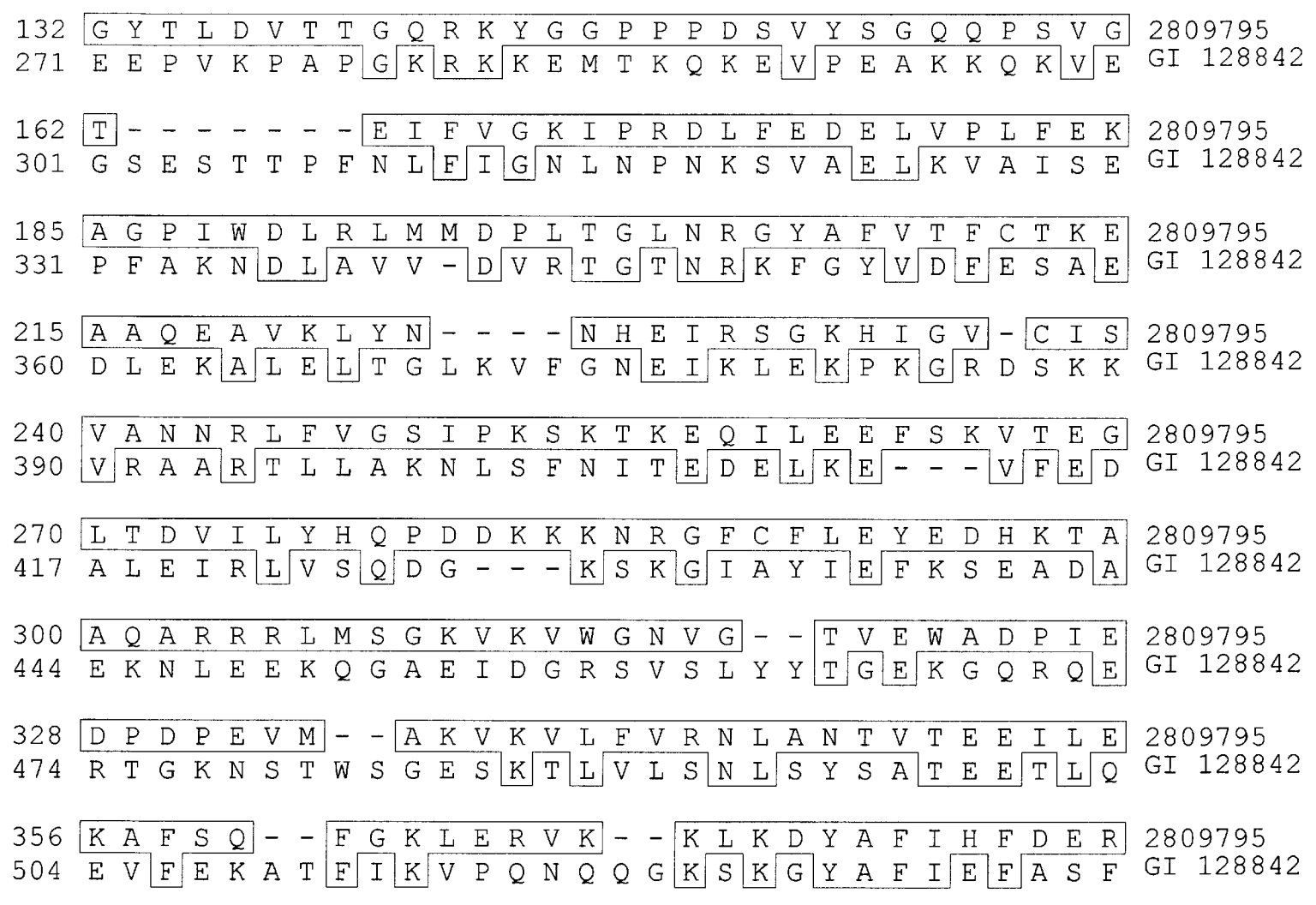

In one embodiment, the invention encompasses a polypeptide comprising the amino acid sequence of SEQ ID NO:1, as shown in FIGS. 1A, 1B, 1C 1D, 1E, and 1F. HNLP is 546 amino acids in length and has two potential eukaryotic putative RNA-binding region signature sequences, consisting of the sequences $R_{203}$ through $F_{210}$, and $R_{286}$ through $Y_{293}$. In addition, HNLP has a potential amidation site at residue $A_{537}$, potential glycosylation sites at residues $N_9$ and $N_{90}$, and potential casein kinase II phosphorylation sites at residues $T_{29}$, $S_{55}$, and $T_{348}$. HNLP also has potential protein kinase C phosphorylation sites at residues $T_{101}$, $S_{115}$, $S_{230}$, $S_{308}$, $S_{524}$, and $S_{531}$, and potential tyrosine kinase phosphorylation sites at residues $Y_{133}$ and $Y_{485}$. As shown in FIGS. 2A, 2B, and 2C, HNLP has chemical and structural homology with nucleolin (GI 128842; SEQ ID NO:3). In particular, HNLP and hamster nucleolin share 22% identity, as well as sharing one of the potential eukaryotic putative RNA-binding regions signature sequences, the potential casein kinase II phosphorylation sites, and the potential amidation site. Northern analysis shows the expression of this sequence in various libraries, at least 51% of which are immortalized or cancerous and at least 31% of which involve in autoimmune or inflammatory responses. Of particular note is the expression of HNLP in brain tissue from Alzheimer's diseased patients.

The invention also encompasses HNLP variants. A preferred HNLP variant is one which has at least about 80%, more preferably at least about 90%, and most preferably at least about 95% amino acid sequence identity to the HNLP amino acid sequence, and which contains at least one functional or structural characteristic of HNLP.

The invention also encompasses polynucleotides which encode HNLP. In a particular embodiment, the invention encompasses a polynucleotide sequence comprising the sequence of SEQ ID NO:2, which encodes an HNLP.

The invention also encompasses a variant of a polynucleotide sequence encoding HNLP. In particular, such a variant polynucleotide sequence will have at least about 80%, more preferably at least about 90%, and most preferably at least about 95% polynucleotide sequence identity to the polynucleotide sequence encoding HNLP. A particular aspect of the invention encompasses a variant of SEQ ID NO:2 which has at least about 80%, more preferably at least about 90%, and most preferably at least about 95% polynucleotide sequence identity to SEQ ID NO:2. Any one of the polynucleotide variants described above can encode an amino acid sequence which contains at least one functional or structural characteristic of HNLP.

It will be appreciated by those skilled in the art that as a result of the degeneracy of the genetic code, a multitude of polynucleotide sequences encoding HNLP, some bearing minimal homology to the polynucleotide sequences of any known and naturally occurring gene, may be produced. Thus, the invention contemplates each and every possible variation of polynucleotide sequence that could be made by selecting combinations based on possible codon choices. These combinations are made in accordance with the standard triplet genetic code as applied to the polynucleotide sequence of naturally occurring HNLP, and all such variations are to be considered as being specifically disclosed.

Although nucleotide sequences which encode HNLP and its variants are preferably capable of hybridizing to the nucleotide sequence of the naturally occurring HNLP under appropriately selected conditions of stringency, it may be advantageous to produce nucleotide sequences encoding HNLP or its derivatives possessing a substantially different codon usage. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding HNLP and its derivatives without altering the encoded amino acid sequences include the production of RNA transcripts having more desirable properties, such as a greater half-life, than transcripts produced from the naturally occurring sequence.

The invention also encompasses production of DNA sequences which encode HNLP and HNLP derivatives, or fragments thereof, entirely by synthetic chemistry. After production, the synthetic sequence may be inserted into any of the many available expression vectors and cell systems using reagents that are well known in the art. Moreover, synthetic chemistry may be used to introduce mutations into a sequence encoding HNLP or any fragment thereof.

Also encompassed by the invention are polynucleotide sequences that are capable of hybridizing to the claimed polynucleotide sequences, and, in particular, to those shown in SEQ ID NO:2, or a fragment of SEQ ID NO:2, under various conditions of stringency as taught in Wahl, G. M. and S. L. Berger (1987; Methods Enzymol. 152:399–407) and Kimmel, A. R. (1987; Methods Enzymol. 152:507–511).

Methods for DNA sequencing are well known and generally available in the art and may be used to practice any of the embodiments of the invention. The methods may employ such enzymes as the Klenow fragment of DNA polymerase I, SEQUENASE DNA Polymerase (US Biochemical Corp., Cleveland, Ohio), Taq polymerase (Perkin Elmer), thermostable T7 polymerase (Amersham, Chicago, Ill.), or combinations of polymerases and proofreading exonucleases such as those found in the ELONGASE (GIBCO/BRL, amplification system Gaithersburg, Md.). Preferably, the process is automated with machines such as the Hamilton MICROLAB 2200 (Hamilton, Reno, Nev.), Peltier thermal cycler (PTC200; MJ Research, Watertown, Mass.) and the ABI CATALYST and 373 and 377 DNA SEQUENCERS (Perkin Elmer).

The nucleic acid sequences encoding HNLP may be extended utilizing a partial nucleotide sequence and employing various methods known in the art to detect upstream sequences, such as promoters and regulatory elements. For example, one method which may be employed, restriction-site PCR, uses universal primers to retrieve unknown sequence adjacent to a known locus. (Sarkar, G. (1993) PCR Methods Applic. 2:318–322.) In particular, genomic DNA is first amplified in the presence of a primer to a linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

Inverse PCR may also be used to amplify or extend sequences using divergent primers based on a known region. (Triglia, T. et al. (1988) Nucleic Acids Res. 16:8186.) The primers may be designed using commercially available software such as OLIGO 4.06 primer analysis software (National Biosciences Inc., Plymouth, Minn.) or another appropriate program to be about 22 to 30 nucleotides in length, to have a GC content of about 50% or more, and to anneal to the target sequence at temperatures of about 68° C. to 72° C. The method uses several restriction enzymes to generate a suitable fragment in the known region of a gene. The fragment is then circularized by intramolecular ligation and used as a PCR template.

Another method which may be used is capture PCR, which involves PCR amplification of DNA fragments adjacent to a known sequence in human and yeast artificial chromosome DNA. (Lagerstrom, M. et al. (1991) PCR Methods Applic. 1:111–119.) In this method, multiple restriction enzyme digestions and ligations may be used to place an engineered double-stranded sequence into an unknown fragment of the DNA molecule before performing PCR. Another method which may be used to retrieve unknown sequences is that of Parker, J. D. et al. (1991; Nucleic Acids Res. 19:3055–3060). Additionally, one may use PCR, nested primers, and PROMOTERFINDER™ libraries to walk genomic DNA (Clontech, Palo Alto, Calif.). This process avoids the need to screen libraries and is useful in finding intron/exon junctions.

When screening for full-length cDNAs, it is preferable to use libraries that have been size-selected to include larger cDNAs. Also, random-primed libraries are preferable in that they will include more sequences which contain the 5' regions of genes. Use of a randomly primed library may be especially preferable for situations in which an oligo d(T) library does not yield a full-length cDNA. Genomic libraries may be useful for extension of sequence into 5' non-transcribed regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different fluorescent dyes (one for each nucleotide) which are laser activated, and a charge coupled device camera for detection of the emitted wavelengths. Output/light intensity may be converted to electrical signal using appropriate software (e.g., GENOTYPER and SEQUENCE NAVIGATOR, Perkin Elmer), and the entire process from loading of samples to computer analysis and electronic data display may be computer controlled. Capillary electrophoresis is especially preferable for the sequencing of small pieces of DNA which might be present in limited amounts in a particular sample.

In another embodiment of the invention, polynucleotide sequences or fragments thereof which encode HNLP may be used in recombinant DNA molecules to direct expression of HNLP, or fragments or functional equivalents thereof, in appropriate host cells. Due to the inherent degeneracy of the genetic code, other DNA sequences which encode substantially the same or a functionally equivalent amino acid sequence may be produced, and these sequences may be used to clone and express HNLP.

As will be understood by those of skill in the art, it may be advantageous to produce HNLP-encoding nucleotide sequences possessing non-naturally occurring codons. For example, codons preferred by a particular prokaryotic or eukaryotic host can be selected to increase the rate of protein expression or to produce an RNA transcript having desirable properties, such as a half-life which is longer than that of a transcript generated from the naturally occurring sequence.

The nucleotide sequences of the present invention can be engineered using methods generally known in the art in order to alter HNLP encoding sequences for a variety of reasons including, but not limited to, alterations which modify the cloning, processing, and/or expression of the gene product. DNA shuffling by random fragmentation and PCR reassembly of gene fragments and synthetic oligonucleotides may be used to engineer the nucleotide sequences. For example, site-directed mutagenesis may be used to insert new restriction sites, alter glycosylation patterns, change codon preference, produce splice variants, introduce mutations, and so forth.

In another embodiment of the invention, natural, modified, or recombinant nucleic acid sequences encoding HNLP may be ligated to a heterologous sequence to encode a fusion protein. For example, to screen peptide libraries for inhibitors of HNLP activity, it may be useful to encode a chimeric HNLP protein that can be recognized by a commercially available antibody. A fusion protein may also be engineered to contain a cleavage site located between the HNLP encoding sequence and the heterologous protein sequence, so that HNLP may be cleaved and purified away from the heterologous moiety.

In another embodiment, sequences encoding HNLP may be synthesized, in whole or in part, using chemical methods well known in the art. (See, e.g., Caruthers, M. H. et al. (1980) Nucl. Acids Res. Symp. Ser. 7:215–223, and Horn, T. et al. (1980) Nucl. Acids Res. Symp. Ser. 7:225–232.) Alternatively, the protein itself may be produced using chemical methods to synthesize the amino acid sequence of HNLP, or a fragment thereof. For example, peptide synthesis can be performed using various solid-phase techniques (Roberge, J. Y. et al. (1995) Science 269:202–204) and automated synthesis may be achieved using the ABI 431A PEPTIDE SYNTHESIZER (Perkin Elmer).

The newly synthesized peptide may be substantially purified by preparative high performance liquid chromatography. (See, e.g., Chiez, R. M. and Regnier, F. Z. (1990) Methods Enzymol. 182:392–421.). The composition of the synthetic peptides may be confirmed by amino acid analysis or by sequencing. (See, e.g., the Edman degradation procedure described in Creighton, T. (1983) *Proteins, Structures and Molecular Principles*, WH Freeman and Co., New York, N.Y.). Additionally, the amino acid sequence of HNLP, or any part thereof, may be altered during direct synthesis and/or combined with sequences from other proteins, or any part thereof, to produce a variant polypeptide.

In order to express a biologically active HNLP, the nucleotide sequences encoding HNLP or derivatives thereof may be inserted into appropriate expression vector, i.e., a vector which contains the necessary elements for the transcription and translation of the inserted coding sequence.

Methods which are well known to those skilled in the art may be used to construct expression vectors containing sequences encoding HNLP and appropriate transcriptional and translational control elements. These methods include in vitro recombinant DNA techniques, synthetic techniques, and in vivo genetic recombination. Such techniques are described in Sambrook, J. et al. (1989; *Molecular Cloning, A Laboratory Manual*, ch. 4, 8, and 16–17, Cold Spring Harbor Press, Plainview, N.Y.) and Ausubel, F. M. et al. (1995 and periodic supplements; *Current Protocols in Molecular Biology*, ch. 9, 13, and 16, John Wiley & Sons, New York, N.Y.).

A variety of expression vector/host systems may be utilized to contain and express sequences encoding HNLP. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus (CaMV) or tobacco mosaic virus (TMV)) or with bacterial expression vectors (e.g., Ti or pBR322 plasmids); or animal cell systems. The invention is not limited by the host cell employed.

The "control elements" or "regulatory sequences" are those non-translated regions of the vector (i.e., enhancers, promoters, and 5' and 3' untranslated regions) which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the BLUESCRIPT phagemid (Stratagene, La Jolla, Calif.) or PSPORT1 plasmid (GIBCO/BRL), and the like, may be used. The baculovirus polyhedrin promoter may be used in insect cells. Promoters or enhancers derived from the genomes of plant cells (e.g., heat shock, RUBISCO, and storage protein genes) or from plant viruses (e.g., viral promoters or leader sequences) may be cloned into the vector. In mammalian cell systems, promoters from mammalian genes or from mammalian viruses are preferable. If it is necessary to generate a cell line that contains multiple copies of the sequence encoding HNLP, vectors based on SV40 or EBV may be used with an appropriate selectable marker.

In bacterial systems, a number of expression vectors may be selected depending upon the use intended for HNLP. For example, when large quantities of HNLP are needed for the induction of antibodies, vectors which direct high level expression of fusion proteins that are readily purified may be used. Such vectors include, but are not limited to, multifunctional *E. coli* cloning and expression vectors such as the BLUESCRIPT phagemid (Stratagene), in which the sequence encoding HNLP may be ligated into the vector in frame with sequences for the amino-terminal Met and the subsequent 7 residues of β-galactosidase so that a hybrid protein is produced, pIN vectors (Van Heeke, G. and S. M. Schuster (1989) J. Biol. Chem. 264:5503–5509), and the like. PGEX vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast *Saccharomyces cerevisiae*, a number of vectors containing constitutive or inducible promoters, such as alpha factor, alcohol oxidase, and PGH, may be used. For reviews, see Ausubel (supra) and Grant et al. (1987; Methods Enzymol. 153:516–544).

In cases where plant expression vectors are used, the expression of sequences encoding HNLP may be driven by any of a number of promoters. For example, viral promoters such as the $^{35}$S and 19S promoters of CaMV may be used alone or in combination with the omega leader sequence from TMV. (Takamatsu, N.(1987) EMBO J. 6:307–311.) Alternatively, plant promoters such as the small subunit of RUBISCO or heat shock promoters may be used. (Coruzzi, G. et al. (1984) EMBO J. 3:1671–1680; Broglie, R. et al. (1984) Science 224:838–843; and Winter, J. et al. (1991) Results Probl. Cell Differ. 17:85–105.) These constructs can be introduced into plant cells by direct DNA transformation or pathogen-mediated transfection. Such techniques are described in a number of generally available reviews. (See, for example, Hobbs, S. or Murry, L. E. in *McGraw Hill Yearbook of Science and Technology* (1992) McGraw Hill, New York, N.Y.; pp. 191–196.)

An insect system may also be used to express HNLP. For example, in one such system, *Autographa californica* nuclear polyhedrosis virus (AcNPV) is used as a vector to express foreign genes in *Spodoptera frugiperda* cells or in Trichoplusia larvae. The sequences encoding HNLP may be cloned into a non-essential region of the virus, such as the polyhedrin gene, and placed under control of the polyhedrin promoter. Successful insertion of HNLP will render the polyhedrin gene inactive and produce recombinant virus lacking coat protein. The recombinant viruses may then be used to infect, for example, *S. frugiperda* cells or Trichoplusia larvae in which HNLP may be expressed. (Engelhard, E. K. et al. (1994) Proc. Nat. Acad. Sci. 91:3224–3227.)

In mammalian host cells, a number of viral-based expression systems may be utilized. In cases where an adenovirus is used as an expression vector, sequences encoding HNLP may be ligated into an adenovirus transcription/translation complex consisting of the late promoter and tripartite leader sequence. Insertion in a non-essential E1 or E3 region of the viral genome may be used to obtain a viable virus which is capable of expressing HNLP in infected host cells. (Logan, J. and T. Shenk (1984) Proc. Natl. Acad. Sci. 81:3655–3659.) In addition, transcription enhancers, such as the Rous sarcoma virus (RSV) enhancer, may be used to increase expression in mammalian host cells.

Human artificial chromosomes (HACs) may also be employed to deliver larger fragments of DNA than can be contained and expressed in a plasmid. HACs of about 6 Mb to 10 Mb are constructed and delivered via conventional delivery methods (liposomes, polycationic amino polymers, or vesicles) for therapeutic purposes.

Specific initiation signals may also be used to achieve more efficient translation of sequences encoding HNLP. Such signals include the ATG initiation codon and adjacent sequences. In cases where sequences encoding HNLP and its initiation codon and upstream sequences are inserted into the appropriate expression vector, no additional transcriptional or translational control signals may be needed. However, in cases where only coding sequence, or a fragment thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers appropriate for the particular cell system used, such as those described in the literature. (Scharf, D. et al. (1994) Results Probl. Cell Differ. 20:125–162.)

In addition, a host cell strain may be chosen for its ability to modulate expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding, and/or function. Different host cells which have specific cellular machinery and characteristic mechanisms for post-translational activities (e.g., CHO, HeLa, MDCK, HEK293, and W138), are available from the American Type Culture Collection (ATCC, Bethesda, Md.) and may be chosen to ensure the correct modification and processing of the foreign protein.

For long term, high yield production of recombinant proteins, stable expression is preferred. For example, cell lines capable of stably expressing HNLP can be transformed using expression vectors which may contain viral origins of replication and/or endogenous expression elements and a selectable marker gene on the same or on a separate vector. Following the introduction of the vector, cells may be allowed to grow for about 1 to 2 days in enriched media before being switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase genes (Wigler, M. et al. (1977) Cell 11:223–32) and adenine phosphoribosyltransferase genes (Lowy, I. et al. (1980) Cell 22:817–23), which can be employed in tk$^-$ or apr$^-$ cells, respectively. Also, antimetabolite, antibiotic, or herbicide resistance can be used as the basis for selection. For example, dhfr confers resistance to methotrexate (Wigler, M. et al. (1980) Proc. Natl. Acad. Sci. 77:3567–70); npt confers resistance to the aminoglycosides neomycin and G-418 (Colbere-Garapin, F. et al (1981) J. Mol. Biol. 150:1–14); and als or pat confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine. (Hartman, S. C. and R. C. Mulligan (1988) Proc. Natl. Acad. Sci. 85:8047–51.) Recently, the use of visible markers has gained popularity with such markers as anthocyanins, β glucuronidase and its substrate GUS, and luciferase and its substrate luciferin. These markers can be used not only to identify transformants, but also to quantify the amount of transient or stable protein expression attributable to a specific vector system. (Rhodes, C. A. et al. (1995) Methods Mol. Biol. 55:121–131.)

Although the presence/absence of marker gene expression suggests that the gene of interest is also present, the presence and expression of the gene may need to be confirmed. For example, if the sequence encoding HNLP is inserted within a marker gene sequence, transformed cells containing sequences encoding HNLP can be identified by the absence of marker gene function. Alternatively, a marker gene can be placed in tandem with a sequence encoding HNLP under the control of a single promoter. Expression of the marker gene in response to induction or selection usually indicates expression of the tandem gene as well.

Alternatively, host cells which contain the nucleic acid sequence encoding HNLP and express HNLP may be identified by a variety of procedures known to those of skill in the art. These procedures include, but are not limited to, DNA—DNA or DNA-RNA hybridizations and protein bioassay or immunoassay techniques which include membrane, solution, or chip based technologies for the detection and/or quantification of nucleic acid or protein sequences.

The presence of polynucleotide sequences encoding HNLP can be detected by DNA—DNA or DNA-RNA hybridization or amplification using probes or fragments or fragments of polynucleotides encoding HNLP. Nucleic acid amplification based assays involve the use of oligonucleotides or oligomers based on the sequences encoding HNLP to detect transformants containing DNA or RNA encoding HNLP.

A variety of protocols for detecting and measuring the expression of HNLP, using either polyclonal or monoclonal antibodies specific for the protein, are known in the art. Examples of such techniques include enzyme-linked immunosorbent assays (ELISAs), radioimmunoassays (RIAs), and fluorescence activated cell sorting (FACS). A two-site, monoclonal-based immunoassay utilizing monoclonal antibodies reactive to two non-interfering epitopes on HNLP is preferred, but a competitive binding assay may be employed. These and other assays are well described in the art, for example, in Hampton, R. et al. (1990; *Serological Methods, a Laboratory Manual*, Section IV, APS Press, St Paul, Minn.) and in Maddox, D. E. et al. (1983; J. Exp. Med. 158:1211–1216).

A wide variety of labels and conjugation techniques are known by those skilled in the art and may be used in various nucleic acid and amino acid assays. Means for producing labeled hybridization or PCR probes for detecting sequences related to polynucleotides encoding HNLP include oligolabeling, nick translation, end-labeling, or PCR amplification using a labeled nucleotide. Alternatively, the sequences encoding HNLP, or any fragments thereof, may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits, such as those provided by Pharmacia & Upjohn (Kalamazoo, Mich.), Promega (Madison, Wis.), and U.S. Biochemical Corp. (Cleveland, Ohio). Suitable reporter molecules or labels which may be used for ease of detection include radionuclides, enzymes, fluorescent, chemiluminescent, or chromogenic agents, as well as substrates, cofactors, inhibitors, magnetic particles, and the like.

Host cells transformed with nucleotide sequences encoding HNLP may be cultured under conditions suitable for the expression and recovery of the protein from cell culture. The protein produced by a transformed cell may be secreted or contained intracellularly depending on the sequence and/or the vector used. As will be understood by those of skill in the art, expression vectors containing polynucleotides which encode HNLP may be designed to contain signal sequences which direct secretion of HNLP through a prokaryotic or eukaryotic cell membrane. Other constructions may be used to join sequences encoding HNLP to nucleotide sequences encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAG extension/affinity purification system (Immunex Corp., Seattle, Wash.). The inclusion of cleavable linker sequences, such as those specific for Factor XA or enterokinase (Invitrogen, San Diego, Calif.), between the purification domain and the HNLP encoding sequence may be used to facilitate purification. One such expression vector provides for expression of a fusion protein containing HNLP and a nucleic acid encoding 6 histidine residues preceding a thioredoxin or an enterokinase cleavage site. The histidine residues facilitate purification on immobilized metal ion affinity chromatography (IMIAC; described in Porath, J. et al. (1992) Prot. Exp. Purif. 3: 263–281)), while the enterokinase cleavage site provides a means for purifying HNLP from the fusion protein. A discussion of vectors which contain fusion proteins is provided in Kroll, D. J. et al. (1993; DNA Cell Biol. 12:441–453).

Fragments of HNLP may be produced not only by recombinant production, but also by direct peptide synthesis using solid-phase techniques. (Merrifield J. (1963) J. Am. Chem. Soc. 85:2149–2154.) Protein synthesis may be performed by manual techniques or by automation. Automated synthesis may be achieved, for example, using the Applied Biosystems 431A peptide synthesizer (Perkin Elmer). Various fragments of HNLP may be synthesized separately and then combined to produce the full length molecule.

THERAPEUTICS

Chemical and structural homology exists between HNLP and nucleolin from hamster (GI 128842). In addition, HNLP is expressed in cancerous tissue and in tissues involved with the autoimmune response. Therefore, HNLP appears to play a role in cancer, autoimmune disorders, and Alzheimer's disease.

Therefore, in one embodiment, an antagonist of HNLP may be administered to a subject to treat or prevent a cancer. Such a cancer may include, but is not limited to, adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus. In one aspect, an antibody which specifically binds HNLP may be used directly as an antagonist or indirectly as a targeting or delivery mechanism for bringing a pharmaceutical agent to cells or tissue which express HNLP.

In an additional embodiment, a vector expressing the complement of the polynucleotide encoding HNLP may be administered to a subject to treat or prevent a cancer including, but not limited to, those described above.

In a further embodiment, an antagonist of HNLP may be administered to a subject to treat or prevent an autoimmune disorder. Such a disorder may include, but is not limited to, AIDS, Addison's disease, adult respiratory distress syndrome, allergies, ankylosing spondylitis, amyloidosis, anemia, asthma, atherosclerosis, autoimmune hemolytic anemia, autoimmune thyroiditis, bronchitis, cholecystitis, chronic graft-versus-host disease, contact dermatitis, Crohn's disease, atopic dermatitis, dermatomyositis, diabetes mellitus, emphysema, erythema nodosum, atrophic gastritis, glomerulonephritis, Goodpasture's syndrome, gout, Graves' disease, Hashimoto's thyroiditis, hypereosinophilia, irritable bowel syndrome, lupus erythematosus, multiple sclerosis, myasthenia gravis, myocardial or pericardial inflammation, osteoarthritis, osteoporosis, pancreatitis, polymyositis, rheumatoid arthritis, scleroderma, Sjögren's syndrome, systemic anaphylaxis, systemic lupus erythematosus, systemic sclerosis, ulcerative colitis, Werner syndrome, and complications of cancer, hemodialysis, and extracorporeal circulation; viral, bacterial, fungal, parasitic, protozoal, and helminthic infections; and trauma. In one aspect, an antibody which specifically binds HNLP may be used directly as an antagonist or indirectly as a targeting or delivery mechanism for bringing a pharmaceutical agent to cells or tissue which express HNLP.

In an additional embodiment, a vector expressing the complement of the polynucleotide encoding HNLP may be administered to a subject to treat or prevent an autoimmune disorder, including, but not limited to, those described above.

In yet another embodiment, an antagonist of HNLP may be administered to a subject to treat or prevent Alzheimer's disease. In one aspect, an antibody which specifically binds HNLP may be used directly as an antagonist or indirectly as a targeting or delivery mechanism for bringing a pharmaceutical agent to cells or tissue which express HNLP.

In an additional embodiment, a vector expressing the complement of the polynucleotide encoding HNLP may be administered to a subject to treat or prevent Alzheimer's disease.

In other embodiments, any of the proteins, antagonists, antibodies, agonists, complementary sequences, or vectors of the invention may be administered in combination with other appropriate therapeutic agents. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

An antagonist of HNLP may be produced using methods which are generally known in the art. In particular, purified HNLP may be used to produce antibodies or to screen libraries of pharmaceutical agents to identify those which specifically bind HNLP. Antibodies to HNLP may also be generated using methods that are well known in the art. Such antibodies may include, but are not limited to, polyclonal, monoclonal, chimeric, and single chain antibodies, Fab fragments, and fragments produced by a Fab expression library. Neutralizing antibodies (i.e., those which inhibit dimer formation) are especially preferred for therapeutic use.

For the production of antibodies, various hosts including goats, rabbits, rats, mice, humans, and others may be immunized by injection with HNLP or with any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, KLH, and dinitrophenol. Among adjuvants used in humans, BCG (bacilli Calmette-Guerin) and *Corynebacterium parvum* are especially preferable.

It is preferred that the oligopeptides, peptides, or fragments used to induce antibodies to HNLP have an amino acid sequence consisting of at least about 5 amino acids, and, more preferably, of at least about 10 amino acids. It is also preferable that these oligopeptides, peptides, or fragments are identical to a portion of the amino acid sequence of the natural protein and contain the entire amino acid sequence of a small, naturally occurring molecule. Short stretches of HNLP amino acids may be fused with those of another protein, such as KLH, and antibodies to the chimeric molecule may be produced.

Monoclonal antibodies to HNLP may be prepared using any technique which provides for the production of antibody molecules by continuous cell lines in culture. These include, but are not limited to, the hybridoma technique, the human B-cell hybridoma technique, and the EBV-hybridoma technique. (Kohler, G. et al. (1975) Nature 256:495–497; Kozbor, D. et al. (1985) J. Immunol. Methods 81:31–42; Cote, R. J. et al. (1983) Proc. Natl. Acad. Sci. 80:2026–2030; and Cole, S. P. et al. (1984) Mol. Cell Biol. 62:109–120.)

In addition, techniques developed for the production of "chimeric antibodies," such as the splicing of mouse antibody genes to human antibody genes to obtain a molecule with appropriate antigen specificity and biological activity, can be used. (Morrison, S. L. et al. (1984) Proc. Natl. Acad. Sci. 81:6851–6855; Neuberger, M. S. et al. (1984) Nature 312:604–608; and Takeda, S. et al. (1985) Nature 314:452–454.) Alternatively, techniques described for the production of single chain antibodies may be adapted, using methods known in the art, to produce HNLP-specific single chain antibodies. Antibodies with related specificity, but of distinct idiotypic composition, may be generated by chain shuffling from random combinatorial immunoglobulin libraries. (Burton D. R. (1991) Proc. Natl. Acad. Sci. 88:11120–11123.)

Antibodies may also be produced by inducing in vivo production in the lymphocyte population or by screening immunoglobulin libraries or panels of highly specific binding reagents as disclosed in the literature. (Orlandi, R. et al. (1989) Proc. Natl. Acad. Sci. 86: 3833–3837, and Winter, G. et al. (1991) Nature 349:293–299.)

Antibody fragments which contain specific binding sites for HNLP may also be generated. For example, such fragments include, but are not limited to, F(ab')2 fragments produced by pepsin digestion of the antibody molecule and Fab fragments generated by reducing the disulfide bridges of the F(ab')2 fragments. Alternatively, Fab expression libraries may be constructed to allow rapid and easy identification of monoclonal Fab fragments with the desired specificity. (Huse, W. D. et al. (1989) Science 254:1275–1281.)

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between HNLP and its specific antibody. A two-site, monoclonal-based immunoassay utilizing monoclonal antibodies reactive to two non-interfering HNLP epitopes is preferred, but a competitive binding assay may also be employed. (Maddox, supra.)

In another embodiment of the invention, the polynucleotides encoding HNLP, or any fragment or complement thereof, may be used for therapeutic purposes. In one aspect, the complement of the polynucleotide encoding HNLP may be used in situations in which it would be desirable to block the transcription of the mRNA. In particular, cells may be transformed with sequences complementary to polynucleotides encoding HNLP. Thus, complementary molecules or fragments may be used to modulate HNLP activity, or to achieve regulation of gene function. Such technology is now well known in the art, and sense or antisense oligonucleotides or larger fragments can be designed from various locations along the coding or control regions of sequences encoding HNLP.

Expression vectors derived from retroviruses, adenoviruses, or herpes or vaccinia viruses, or from various bacterial plasmids, may be used for delivery of nucleotide sequences to the targeted organ, tissue, or cell population. Methods which are well known to those skilled in the art can be used to construct vectors which will express nucleic acid sequence complementary to the polynucleotides of the gene encoding HNLP. These techniques are described, for example, in Sambrook (supra) and in Ausubel (supra).

Genes encoding HNLP can be turned off by transforming a cell or tissue with expression vectors which express high levels of a polynucleotide or fragment thereof encoding HNLP. Such constructs may be used to introduce untranslatable sense or antisense sequences into a cell. Even in the absence of integration into the DNA, such vectors may continue to transcribe RNA molecules until they are disabled by endogenous nucleases. Transient expression may last for a month or more with a non-replicating vector, and may last even longer if appropriate replication elements are part of the vector system.

As mentioned above, modifications of gene expression can be obtained by designing complementary sequences or antisense molecules (DNA, RNA, or PNA) to the control, 5', or regulatory regions of the gene encoding HNLP. Oligonucleotides derived from the transcription initiation site, e.g., between about positions −10 and +10 from the start site, are preferred. Similarly, inhibition can be achieved using triple helix base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature. (Gee, J. E. et al. (1994) in Huber, B. E. and B. I. Carr, *Molecular and Immunologic Approaches*, pp. 163–177, Futura Publishing Co., Mt. Kisco, N.Y.) A complementary sequence or antisense molecule may also be designed to block translation of mRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. For example, engineered hammerhead motif ribozyme molecules specifically and efficiently catalyze endonucleolytic cleavage of sequences encoding HNLP.

Specific ribozyme cleavage sites within any potential RNA target are initially identified by scanning the target molecule for ribozyme cleavage sites, including the following sequences: GUA, GUU, and GUC. Once identified, short RNA sequences of between 15 and 20 ribonucleotides corresponding to the region of the target gene containing the cleavage site may be evaluated for secondary structural features which may render the oligonucleotide inoperable. The suitability of candidate targets may also be evaluated by testing accessibility to hybridization with complementary oligonucleotides using ribonuclease protection assays.

Complementary ribonucleic acid molecules and ribozymes of the invention may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding HNLP. Such DNA sequences may be incorporated into a wide variety of vectors with suitable RNA polymerase promoters such as T7 or SP6. Alternatively, these cDNA constructs that synthesize complementary RNA constitutively or inducibly can be introduced into cell lines, cells, or tissues.

RNA molecules may be modified to increase intracellular stability and half-life. Possible modifications include, but are not limited to, the addition of flanking sequences at the 5' and/or 3' ends of the molecule or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection, by liposome injections, or by polycationic amino polymers may be achieved using methods which are well known in the art, such as those described in Goldman, C. K. et al. (1997; Nature Biotechnology 15:462–466).

Any of the therapeutic methods described above may be applied to any subject in need of such therapy, including, for example, mammals such as dogs, cats, cows, horses, rabbits, monkeys, and most preferably, humans.

An additional embodiment of the invention relates to the administration of a pharmaceutical or sterile composition, in conjunction with a pharmaceutically acceptable carrier, for any of the therapeutic effects discussed above. Such pharmaceutical compositions may consist of HNLP, antibodies to HNLP, and mimetics, agonists, antagonists, or inhibitors of HNLP. The compositions may be administered alone or in combination with at least one other agent, such as a stabilizing compound, which may be administered in any sterile, biocompatible pharmaceutical carrier including, but not limited to, saline, buffered saline, dextrose, and water. The compositions may be administered to a patient alone, or in combination with other agents, drugs or hormones.

The pharmaceutical compositions utilized in this invention may be administered by any number of routes including, but not limited to, oral, intravenous, intramuscular, intraarterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of *Remington's Pharmaceutical Sciences* (Maack Publishing Co., Easton, Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combining active compounds with solid excipient and processing the resultant mixture of granules (optionally, after grinding) to obtain tablets or dragee cores. Suitable auxiliaries can be added, if desired. Suitable excipients include carbohydrate or protein fillers, such as sugars, including lactose, sucrose, mannitol, and sorbitol; starch from corn, wheat, rice, potato, or other plants; cellulose, such as methyl cellulose, hydroxypropylmethyl-cellulose, or sodium carboxymethylcellulose; gums, including arabic and tragacanth; and proteins, such as gelatin and collagen. If desired, disintegrating or solubilizing agents may be added, such as the cross-linked polyvinyl pyrrolidone, agar, and alginic acid or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with fillers or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated in aqueous solutions, preferably in physiologically compatible buffers such as Hanks' solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils, such as sesame oil, or synthetic fatty acid esters, such as ethyl oleate, triglycerides, or liposomes. Non-lipid polycationic amino polymers may also be used for delivery. Optionally, the suspension may also contain suitable stabilizers or agents to increase the solubility of the compounds and allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, and succinic acid. Salts tend to be more soluble in aqueous or other protonic solvents than are the corresponding free base forms. In other cases, the preferred preparation may be a lyophilized powder which may contain any or all of the following: 1 mM to 50 mM histidine, 0.1% to 2% sucrose, and 2% to 7% mannitol, at a pH range of 4.5 to 5.5, that is combined with buffer prior to use.

After pharmaceutical compositions have been prepared, they can be placed in an appropriate container and labeled for treatment of an indicated condition. For administration of HNLP, such labeling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays of neoplastic cells, for example, or in animal models, usually mice, rabbits, dogs, or pigs. An animal model may also be used to determine the appropriate concentration range and route of administration. Such information can then be used to determine useful doses and routes for administration in humans.

A therapeutically effective dose refers to that amount of active ingredient, for example HNLP or fragments thereof, antibodies of HNLP, and agonists, antagonists or inhibitors of HNLP, which ameliorates the symptoms or condition. Therapeutic efficacy and toxicity may be determined by standard pharmaceutical procedures in cell cultures or with experimental animals, such as by calculating the ED50 (the dose therapeutically effective in 50% of the population) or LD50 (the dose lethal to 50% of the population) statistics. The dose ratio between therapeutic and toxic effects is the therapeutic index, and it can be expressed as the LD50/ED50 ratio. Pharmaceutical compositions which exhibit large therapeutic indices are preferred. The data obtained from cell culture assays and animal studies is used in formulating a range of dosage for human use. The dosage contained in such compositions is preferably within a range of circulating concentrations that include the ED50 with little or no toxicity. The dosage varies within this range depending upon the dosage form employed, the sensitivity of the patient, and the route of administration.

The exact dosage will be determined by the practitioner, in light of factors related to the subject requiring treatment. Dosage and administration are adjusted to provide sufficient levels of the active moiety or to maintain the desired effect. Factors which may be taken into account include the severity of the disease state, the general health of the subject, the age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on the half-life and clearance rate of the particular formulation.

Normal dosage amounts may vary from 0.1 $\mu$g to 100,000 $\mu$g, up to a total dose of about 1 gram, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

DIAGNOSTICS

In another embodiment, antibodies which specifically bind HNLP may be used for the diagnosis of disorders characterized by expression of HNLP, or in assays to monitor patients being treated with HNLP or agonists, antagonists, and inhibitors of HNLP. Antibodies useful for diagnostic purposes may be prepared in the same manner as those described above for therapeutics. Diagnostic assays for HNLP include methods which utilize the antibody and a label to detect HNLP in human body fluids or in extracts of cells or tissues. The antibodies may be used with or without modification, and may be labeled by covalent or noncovalent joining with a reporter molecule. A wide variety of reporter molecules, several of which are described above, are known in the art and may be used.

A variety of protocols for measuring HNLP, including ELISAs, RIAs, and FACS, are known in the art and provide a basis for diagnosing altered or abnormal levels of HNLP expression. Normal or standard values for HNLP expression are established by combining body fluids or cell extracts taken from normal mammalian subjects, preferably human, with antibody to HNLP under conditions suitable for complex formation. The amount of standard complex formation may be quantified by various methods, preferably by photometric means. Quantities of HNLP expressed in subject, control, and disease samples from biopsied tissues are compared with the standard values. Deviation between standard and subject values establishes the parameters for diagnosing disease.

In another embodiment of the invention, the polynucleotides encoding HNLP may be used for diagnostic purposes. The polynucleotides which may be used include oligonucleotide sequences, complementary RNA and DNA molecules, and PNAs. The polynucleotides may be used to detect and quantitate gene expression in biopsied tissues in which expression of HNLP may be correlated with disease. The diagnostic assay may be used to distinguish between absence, presence, and excess expression of HNLP, and to monitor regulation of HNLP levels during therapeutic intervention.

In one aspect, hybridization with PCR probes which are capable of detecting polynucleotide sequences, including genomic sequences, encoding HNLP or closely related molecules may be used to identify nucleic acid sequences which encode HNLP. The specificity of the probe, whether it is made from a highly specific region (e.g., the 5' regulatory region) or from a less specific region (e.g., the 3' coding region), and the stringency of the hybridization or amplification (maximal, high, intermediate, or low), will determine whether the probe identifies only naturally occurring sequences encoding HNLP, alleles, or related sequences.

Probes may also be used for the detection of related sequences, and should preferably contain at least 50% of the nucleotides from any of the HNLP encoding sequences. The hybridization probes of the subject invention may be DNA or RNA and may be derived from the sequence of SEQ ID NO:2 or from genomic sequences including promoter and enhancer elements and introns of the naturally occurring HNLP.

Means for producing specific hybridization probes for DNAs encoding HNLP include the cloning of polynucleotide sequences encoding HNLP or HNLP derivatives into vectors for the production of mRNA probes. Such vectors are known in the art, are commercially available, and may be used to synthesize RNA probes in vitro by means of the addition of the appropriate RNA polymerases and the appropriate labeled nucleotides. Hybridization probes may be labeled by a variety of reporter groups, for example, by radionuclides such as $^{32}P$ or $^{35}S$, or by enzymatic labels, such as alkaline phosphatase coupled to the probe via avidin/biotin coupling systems, and the like.

Polynucleotide sequences encoding HNLP may be used for the diagnosis of a disorder associated with expression of HNLP. Examples of such a disorder include, but are not limited to, cancers such as adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus; autoimmune disorders such as AIDS, Addison's disease, adult respiratory distress syndrome, allergies, ankylosing spondylitis, amyloidosis, anemia, asthma, atherosclerosis, autoimmune hemolytic anemia, autoimmune thyroiditis, bronchitis, cholecystitis, chronic graft-versus-host disease, contact dermayitis, Crohn's disease, atopic dermatitis, dermatomyositis, diabetes mellitus, emphysema, erythema nodosum, atrophic gastritis, glomerulonephritis, Goodpasture's syndrome, gout, Graves'disease, Hashimoto's thyroiditis, hypereosinophilia, irritable bowel syndrome, lupus erythematosus, multiple sclerosis, myasthenia gravis, myocardial or pericardial inflammation, osteoarthritis, osteoporosis, pancreatitis, polymyositis, rheumatoid arthritis, scleroderma, Sjögren's syndrome, systemic anaphylaxis, systemic lupus erythematosus, systemic sclerosis, ulcerative colitis, Werner syndrome, and complications of cancer, hemodialysis, and extracorporeal circulation; viral, bacterial, fungal, parasitic, protozoal, and helminthic infections; trauma; and Alzheimer's disease. The polynucleotide sequences encoding HNLP may be used in Southern or northern analysis, dot blot, or other membrane-based technologies; in PCR technologies; in dipstick, pin, and ELISA assays; and in microarrays utilizing fluids or tissues from patient biopsies to detect altered HNLP expression. Such qualitative or quantitative methods are well known in the art.

In a particular aspect, the nucleotide sequences encoding HNLP may be useful in assays that detect the presence of associated disorders, particularly those mentioned above. The nucleotide sequences encoding HNLP may be labeled by standard methods and added to a fluid or tissue sample from a patient under conditions suitable for the formation of hybridization complexes. After a suitable incubation period, the sample is washed and the signal is quantitated and compared with a standard value. If the amount of signal in the patient sample is significantly altered from that of a comparable control sample, the nucleotide sequences have hybridized with nucleotide sequences in the sample, and the presence of altered levels of nucleotide sequences encoding HNLP in the sample indicates the presence of the associated disorder. Such assays may also be used to evaluate the efficacy of a particular therapeutic treatment regimen in animal studies, in clinical trials, or in monitoring the treatment of an individual patient.

In order to provide a basis for the diagnosis of a disorder associated with expression of HNLP, a normal or standard profile for expression is established. This may be accomplished by combining body fluids or cell extracts taken from normal subjects, either animal or human, with a sequence, or a fragment thereof, encoding HNLP, under conditions suitable for hybridization or amplification. Standard hybridization may be quantified by comparing the values obtained from normal subjects with values from an experiment in which a known amount of a substantially purified polynucleotide is used. Standard values obtained from normal samples may be compared with values obtained from samples from patients who are symptomatic for a disorder. Deviation from standard values is used to establish the presence of a disorder.

Once the presence of a disorder is established and a treatment protocol is initiated, hybridization assays may be repeated on a regular basis to evaluate whether the level of expression in the patient begins to approximate that which is observed in the normal subject. The results obtained from successive assays may be used to show the efficacy of treatment over a period ranging from several days to months.

With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Additional diagnostic uses for oligonucleotides designed from the sequences encoding HNLP may involve the use of PCR. These oligomers may be chemically synthesized, generated enzymatically, or produced in vitro. Oligomers will preferably contain a fragment of a polynucleotide encoding HNLP, or a fragment of a polynucleotide complementary to the polynucleotide encoding HNLP, and will be employed under optimized conditions for identification of a specific gene or condition. Oligomers may also be employed under less stringent conditions for detection or quantitation of closely related DNA or RNA sequences.

Methods which may also be used to quantitate the expression of HNLP include radiolabeling or biotinylating nucleotides, coamplification of a control nucleic acid, and interpolating results from standard curves. (Melby, P. C. et al. (1993) J. Immunol. Methods 159:235–244, and Duplaa, C. et al. (1993) Anal. Biochem. 212:229–236.) The speed of quantitation of multiple samples may be accelerated by running the assay in an ELISA format where the oligomer of interest is presented in various dilutions and a spectrophotometric or calorimetric response gives rapid quantitation.

In further embodiments, oligonucleotides or longer fragments derived from any of the polynucleotide sequences described herein may be used as targets in a microarray. The microarray can be used to monitor the expression level of large numbers of genes simultaneously (to produce a transcript image) and to identify genetic variants, mutations, and polymorphisms. This information may be used in determining gene function, in understanding the genetic basis of a disorder, in diagnosing a disorder, and in developing and monitoring the activities of therapeutic agents.

In one embodiment, the microarray is prepared and used according to methods known in the art, such as those described in published PCT application WO95/11995 (Chee et al.), Lockhart, D. J. et al. (1996; Nat. Biotech. 14:1675–1680), and Schena, M. et al. (1996; Proc. Natl. Acad. Sci. 93:10614–10619).

The microarray is preferably composed of a large number of unique single-stranded nucleic acid sequences, usually either synthetic antisense oligonucleotides or fragments of cDNAs, fixed to a solid support. The oligonucleotides are preferably about 6 to 60 nucleotides in length, more preferably about 15 to 30 nucleotides in length, and most preferably about 20 to 25 nucleotides in length. For a certain type of microarray, it may be preferable to use oligonucleotides which are about 7 to 10 nucleotides in length. The microarray may contain oligonucleotides which cover the known 5' or 3' sequence, or may contain sequential oligonucleotides which cover the full length sequence or unique oligonucleotides selected from particular areas along the length of the sequence. Polynucleotides used in the microarray may be oligonucleotides specific to a gene or genes of interest in which at least a fragment of the sequence is known or oligonucleotides specific to one or more unidentified cDNAs common to a particular cell or tissue type or to a normal, developmental, or disease state. In certain situations, it may be appropriate to use pairs of oligonucleotides on a microarray. The pairs will be identical, except for one nucleotide preferably located in the center of the sequence. The second oligonucleotide in the pair (mismatched by one) serves as a control. The number of oligonucleotide pairs may range from about 2 to 1,000,000.

In order to produce oligonucleotides to a known sequence for a microarray, the gene of interest is examined using a computer algorithm which starts at the 5' end, or, more preferably, at the 3' end of the nucleotide sequence. The algorithm identifies oligomers of defined length that are unique to the gene, have a GC content within a range suitable for hybridization, and lack predicted secondary structure that may interfere with hybridization. In one aspect, the oligomers are synthesized at designated areas on a substrate using a light-directed chemical process. The substrate may be paper, nylon, any other type of membrane, filter, chip, glass slide, or any other suitable solid support.

In one aspect, the oligonucleotides may be synthesized on the surface of the substrate by using a chemical coupling procedure and an ink jet application apparatus, such as that described in published PCT application WO95/251116 (Baldeschweiler et al.). In another aspect, a grid array analogous to a dot or slot blot (HYBRIDOT® apparatus, GIBCO/BRL) may be used to arrange and link cDNA fragments or oligonucleotides to the surface of a substrate using a vacuum system or thermal, UV, mechanical or chemical bonding procedures. In yet another aspect, an array may be produced by hand or by using available devices, materials, and machines (including Brinkmann® multichannel pipettors or robotic instruments), and may contain 8, 24, 96, 384, 1536, or 6144 oligonucleotides, or any other multiple from 2 to 1,000,000 which lends itself to the efficient use of commercially available instrumentation.

In order to conduct sample analysis using the microarrays, polynucleotides are extracted from a biological sample. The biological samples may be obtained from any bodily fluid (blood, urine, saliva, phlegm, gastric juices, etc.), cultured cells, biopsies, or other tissue preparations. To produce probes, the polynucleotides extracted from the sample are used to produce nucleic acid sequences which are complementary to the nucleic acids on the microarray. If the microarray consists of cDNAs, antisense RNAs (aRNA) are appropriate probes. Therefore, in one aspect, mRNA is used to produce cDNA which, in turn and in the presence of fluorescent nucleotides, is used to produce fragment or oligonucleotide aRNA probes. These fluorescently labeled probes are incubated with the microarray so that the probe sequences hybridize to the cDNA oligonucleotides of the microarray. In another aspect, nucleic acid sequences used as probes can include polynucleotides, fragments, and complementary or antisense sequences produced using restriction enzymes, PCR technologies, and OLIGOLABELING or TRANSPROBE kits (Pharmacia & Upjohn) well known in the area of hybridization technology.

Incubation conditions are adjusted so that hybridization occurs with precise complementary matches or with various degrees of less complementarity. After removal of nonhybridized probes, a scanner is used to determine the levels and patterns of fluorescence. The scanned images are examined to determine the degree of complementarity and the relative abundance of each oligonucleotide sequence on the microarray. A detection system may be used to measure the absence, presence, and amount of hybridization for all of the distinct sequences simultaneously. This data may be used for large scale correlation studies or for functional analysis of the sequences, mutations, variants, or polymorphisms among samples. (Heller, R. A. et al. (1997) Proc. Natl. Acad. Sci. 94:2150–2155.)

In another embodiment of the invention, nucleic acid sequences encoding HNLP may be used to generate hybridization probes useful for mapping the naturally occurring genomic sequence. The sequences may be mapped to a particular chromosome, to a specific region of a chromosome, or to artificial chromosome constructions, such as human artificial chromosomes (HACs), yeast artificial chromosomes (YACs), bacterial artificial chromosomes (BACs), bacterial P1 constructions, or single chromosome cDNA libraries, such as those reviewed in Price, C. M. (1993; Blood Rev. 7:127–134) and Trask, B. J. (1991; Trends Genet. 7:149–154).

Fluorescent in situ hybridization (FISH, as described, e.g., in Heinz-Ulrich, et al. (1995) in Meyers, R. A. (ed.) *Molecular Biology and Biotechnology*, pp. 965–968, VCH Publishers New York, N.Y.) may be correlated with other physical chromosome mapping techniques and genetic map data. Examples of genetic map data can be found in various scientific journals or at the Online Mendelian Inheritance in Man (OMIM) site. Correlation between the location of the gene encoding HNLP on a physical chromosomal map and a specific disorder, or predisposition to a specific disorder, may help define the region of DNA associated with that disorder. The nucleotide sequences of the subject invention may be used to detect differences in gene sequences between normal, carrier, and affected individuals.

In situ hybridization of chromosomal preparations and physical mapping techniques, such as linkage analysis using established chromosomal markers, may be used for extending genetic maps. Often the placement of a gene on the chromosome of another mammalian species, such as mouse, may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once the disease or syndrome has been crudely localized by genetic linkage to a particular genomic region, for example, AT to 11q22-23 (Gatti, R. A. et al. (1988) Nature 336:577–580), any sequences mapping to that area may represent associated or regulatory genes for further investigation. The nucleotide sequence of the subject invention may also be used to detect differences in the chromosomal location due to translocation, inversion, etc., among normal, carrier, or affected individuals.

In another embodiment of the invention, HNLP, its catalytic or immunogenic fragments, or oligopeptides thereof can be used for screening libraries of compounds in any of a variety of drug screening techniques. The fragment employed in such screening may be free in solution, affixed to a solid support, borne on a cell surface, or located intracellularly. The formation of binding complexes between HNLP and the agent being tested may be measured.

Another technique for drug screening which may be used provides for high throughput screening of compounds having suitable binding affinity to the protein of interest as described in published PCT application WO84/03564 (Geysen, et al.). In this method, large numbers of different small test compounds are synthesized on a solid substrate, such as plastic pins or some other surface. The test compounds are reacted with HNLP, or fragments thereof, and washed. Bound HNLP is then detected by methods well known in the art. Purified HNLP can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding HNLP specifically compete with a test compound for binding HNLP. In this manner, antibodies can be used to detect the presence of any peptide which shares one or more antigenic determinants with HNLP.

In additional embodiments, the nucleotide sequences which encode HNLP may be used in any molecular biology techniques that have yet to be developed, provided the new techniques rely on properties of nucleotide sequences that are currently known, including, but not limited to, such properties as the triplet genetic code and specific base pair interactions.

The examples below are provided to illustrate the subject invention and are not included for the purpose of limiting the invention.

EXAMPLES

I. TLYMNOT05 cDNA Library Construction

The lymphocyte cDNA library was constructed from nonactivated Th2 cells. These cells were differentiated from umbilical cord CD4 T cells with IL-4 in the presence of anti-IL-12 antibodies and B7-transfected COS cells. The cells were incubated at a density of $1 \times 10^6$/ml, cultured for 96 hours in DME containing 10% human serum, washed in PBS, scraped and lysed immediately in buffer containing guanidinium isothiocyanate. The lysate was extracted twice with a mixture of phenol and chloroform, pH 8.0 and centrifuged over a CsCl cushion using an Beckman SW28 rotor in a L8–70M Ultracentrifuge (Beckman Instruments). The RNA was precipitated using 0.3M sodium acetate and 2.5 volumes of ethanol, resuspended in water and DNase treated for 15 min at 37° C. The total RNA was isolated using the OLIGOTEX kit (QIAGEN), and used to make cDNAs. The cDNAs were ligated into the pINCY vector (Incyte).

II. Isolation and Sequencing of cDNA Clones

Plasmid DNA was released from the cells and purified using the REAL PREP 96-well plasmid purification kit (Catalog # 26173; QIAGEN).The recommended protocol was employed except for the following changes: 1) the bacteria were cultured in 1 ml of sterile Terrific Broth (Catalog #22711, GIBCO/BRL) with carbenicillin at 25 mg/L and glycerol at 0.4%; 2) after inoculation, the cultures were incubated for 19 hours and at the end of incubation, the cells were lysed with 0.3 ml of lysis buffer; and 3) following isopropanol precipitation, the plasmid DNA pellet was resuspended in 0.1 ml of distilled water. After the last step in the protocol, samples were transferred to a 96-well block for storage at 4° C.

The cDNAs were sequenced by the method of Sanger et al. (1975, J. Mol. Biol. 94: 441 f), using a Hamilton MICROLAB 2200 (Hamilton, Reno, Nev.) in combination with Peltier thermal cyclers (PTC200 from MJ Research, Watertown, Mass.) and Applied Biosystems 377 DNA Sequencing Systems.

III. Homology Searching of cDNA Clones and Their Deduced Proteins

The nucleotide sequences and/or amino acid sequences of the Sequence Listing were used to query sequences in the GenBank, SwissProt, BLOCKS, and Pima II databases. These databases, which contain previously identified and annotated sequences, were searched for regions of homology using BLAST (Basic Local Alignment Search Tool). (Altschul, S. F. (1993) J. Mol. Evol 36:290–300; and Altschul et al. (1990) J. Mol. Biol. 215:403–410.)

BLAST produced alignments of both nucleotide and amino acid sequences to determine sequence similarity. Because of the local nature of the alignments, BLAST was especially useful in determining exact matches or in identifying homologs which may be of prokaryotic (bacterial) or eukaryotic (animal, fungal, or plant) origin. Other algorithms such as the one described in Smith, T. et al. (1992; Protein Engineering 5:35–51), could have been used when dealing with primary sequence patterns and secondary structure gap penalties. The sequences disclosed in this application have lengths of at least 49 nucleotides and have no more than 12% uncalled bases (where N is recorded rather than A, C, G, or T).

The BLAST approach searched for matches between a query sequence and a database sequence. BLAST evaluated the statistical significance of any matches found, and reported only those matches that satisfy the user-selected threshold of significance. In this application, threshold was set at $10^{-25}$ for nucleotides and $10^{-10}$ for peptides.

Incyte nucleotide sequences were searched against the GenBank databases for primate (pri), rodent (rod), and other mammalian sequences (mam), and deduced amino acid sequences from the same clones were then searched against GenBank functional protein databases, mammalian (mamp), vertebrate (vrtp), and eukaryote (eukp), for homology.

IV. Northern Analysis

Northern analysis is a laboratory technique used to detect the presence of a transcript of a gene and involves the hybridization of a labeled nucleotide sequence to a membrane on which RNAs from a particular cell type or tissue have been bound. (Sambrook, supra, ch. 7) and Ausubel, F. M. et al. (supra, ch. 4 and 16).

Analogous computer techniques applying BLAST are used to search for identical or related molecules in nucleotide databases such as GenBank or the LIFESEQ™ database (Incyte Pharmaceuticals). This analysis is much faster than multiple membrane-based hybridizations. In addition, the sensitivity of the computer search can be modified to determine whether any particular match is categorized as exact or homologous.

The basis of the search is the product score, which is defined as:

$$\frac{\% \text{ sequence identity} \times \% \text{ maximum BLAST score}}{100}$$

The product score takes into account both the degree of similarity between two sequences and the length of the sequence match. For example, with a product score of 40, the match will be exact within a 1% to 2% error, and, with a product score of 70, the match will be exact. Homologous molecules are usually identified by selecting those which show product scores between 15 and 40, although lower scores may identify related molecules.

The results of northern analysis are reported as a list of libraries in which the transcript encoding HNLP occurs. Abundance and percent abundance are also reported. Abundance directly reflects the number of times a particular transcript is represented in a cDNA library, and percent abundance is abundance divided by the total number of sequences examined in the cDNA library.

V. Extension of HNLP Encoding Polynucleotides

The nucleic acid sequence of Incyte Clone 2809795 was used to design oligonucleotide primers for extending a partial nucleotide sequence to full length. One primer was synthesized to initiate extension of an antisense polynucleotide, and the other was synthesized to initiate extension of a sense polynucleotide. Primers were used to facilitate the extension of the known sequence "outward" generating amplicons containing new unknown nucleotide sequence for the region of interest. The initial primers were designed from the cDNA using OLIGO 4.06 primer ananlysis software (National Biosciences), or another appropriate program, to be about 22 to 30 nucleotides in length, to have a GC content of about 50% or more, and to anneal to the target sequence at temperatures of about 68° C. to about 72° C. Any stretch of nucleotides which would result in hairpin structures and primer-primer dimerizations was avoided.

Selected human CDNA libraries (GIBCO/BRL) were used to extend the sequence. If more than one extension is necessary or desired, additional sets of primers are designed to further extend the known region.

High fidelity amplification was obtained by following the instructions for the XL-PCR kit (Perkin Elmer) and thoroughly mixing the enzyme and reaction mix. PCR was performed using the Peltier thermal cycler (PTC200; M. J. Research, Watertown, Mass.), beginning with 40 pmol of each primer and the recommended concentrations of all other components of the kit, with the following parameters:

| Step 1 | 94° C. for 1 min (initial denaturation) |
|---|---|
| Step 2 | 65° C. for 1 min |
| Step 3 | 68° C. for 6 min |
| Step 4 | 94° C. for 15 sec |
| Step 5 | 65° C. for 1 min |
| Step 6 | 68° C. for 7 min |
| Step 7 | Repeat steps 4 through 6 for an additional 15 cycles |
| Step 8 | 94° C. for 15 sec |
| Step 9 | 65° C. for 1 min |
| Step 10 | 68° C. for 7:15 min |
| Step 11 | Repeat steps 8 through 10 for an additional 12 cycles |
| Step 12 | 72° C. for 8 min |
| Step 13 | 4° C. (and holding) |

A 5 μl to 10 μl aliquot of the reaction mixture was analyzed by electrophoresis on a low concentration (about 0.6% to 0.8%) agarose mini-gel to determine which reactions were successful in extending the sequence. Bands thought to contain the largest products were excised from the gel, purified using QIAQUICK DNA gel purification kit (QIAGEN Inc., Chatsworth, Calif.), and trimmed of overhangs using Klenow enzyme to facilitate religation and cloning.

After ethanol precipitation, the products were redissolved in 13 μl of ligation buffer, 1 μl T4-DNA ligase (15 units) and 1 μl T4 polynucleotide kinase were added, and the mixture was incubated at room temperature for 2 to 3 hours, or overnight at 16° C. Competent *E. coli* cells (in 40 μl of appropriate media) were transformed with 3 μl of ligation mixture and cultured in 80 μl of SOC medium. (Sambrook, supra, Appendix A, p. 2.). After incubation for one hour at 37° C., the *E. coli* mixture was plated on Luria Bertani (LB) agar (Sambrook, supra, Appendix A, p. 1) containing 2× Carb. The following day, several colonies were randomly picked from each plate and cultured in 150 μl of liquid LB/2× Carb medium placed in an individual well of an appropriate commercially-available sterile 96-well microtiter plate. The following day, 5 μl of each overnight culture was transferred into a non-sterile 96-well plate and, after dilution 1:10 with water, 5 μl from each sample was transferred into a PCR array.

For PCR amplification, 18 μl of concentrated PCR reaction mix (3.3×) containing 4 units of rTth DNA polymerase, a vector primer, and one or both of the gene specific primers used for the extension reaction were added to each well. Amplification was performed using the following conditions:

| Step 1 | 94° C. for 60 sec |
|---|---|
| Step 2 | 94° C. for 20 sec |
| Step 3 | 55° C. for 30 sec |
| Step 4 | 72° C. for 90 sec |
| Step 5 | Repeat steps 2 through 4 for an additional 29 cycles |
| Step 6 | 72° C. for 180 sec |
| Step 7 | 4° C. (and holding) |

Aliquots of the PCR reactions were run on agarose gels together with molecular weight markers. The sizes of the PCR products were compared to the original partial cDNAs, and appropriate clones were selected, ligated into plasmid, and sequenced.

In like manner, the nucleotide sequence of SEQ ID NO:2 is used to obtain 5' regulatory sequences using the procedure above, oligonucleotides designed for 5' extension, and an appropriate genomic library.

VI. Labeling and Use of Individual Hybridization Probes

Hybridization probes derived from SEQ ID NO:2 are employed to screen cDNAs, genomic DNAs, or mRNAs.

Although the labeling of oligonucleotides, consisting of about 20 base pairs, is specifically described, essentially the same procedure is used with larger nucleotide fragments. Oligonucleotides are designed using state-of-the-art software such as OLIGO 4.06 primer analysis software (National Biosciences) and labeled by combining 50 pmol of each oligomer and 250 µCi of [γ-$^{32}$P] adenosine triphosphate (Amersham) and T4 polynucleotide kinase (DuPont NEN®, Boston, Mass.). The labeled oligonucleotides are substantially purified using a SEPHADEX G-25 superfine resin column (Pharmacia & Upjohn). An aliquot containing $10^7$ counts per minute of the labeled probe is used in a typical membrane-based hybridization analysis of human genomic DNA digested with one of the following endonucleases: Ase I, Bgl II, Eco RI, Pst I, Xba 1, or Pvu II (DuPont NEN®).

The DNA from each digest is fractionated on a 0.7 percent agarose gel and transferred to nylon membranes (NYTRAN PLUS membrane, Schleicher & Schuell, Durham, N.H.). Hybridization is carried out for 16 hours at 40° C. To remove nonspecific signals, blots are sequentially washed at room temperature under increasingly stringent conditions up to 0.1× saline sodium citrate and 0.5% sodium dodecyl sulfate. After XOMAT AR autoradiography film (Kodak, Rochester, N.Y.) is exposed to the blots, or the blots are placed in a PHOSPHOIMAGER cassette (Molecular Dynamics, Sunnyvale, Calif.) for several hours, hybridization patterns are compared visually.

VII. Microarrays

To produce oligonucleotides for a microarray, one of the nucleotide sequences of the present invention is examined using a computer algorithm which starts at the 3' end of the nucleotide sequence. The algorithm identifies oligomers of defined length that are unique to the gene, have a GC content within a range suitable for hybridization, and lack predicted secondary structure that would interfere with hybridization. The algorithm identifies approximately 20 sequence-specific oligonucleotides of 20 nucleotides in length (20-mers). A matched set of oligonucleotides are created in which one nucleotide in the center of each sequence is altered. This process is repeated for each gene in the microarray, and double sets of twenty 20-mers are synthesized and arranged on the surface of the silicon chip using a light-directed chemical process, such as that described in Chee (supra).

In the alternative, a chemical coupling procedure and an ink jet device are used to synthesize oligomers on the surface of a substrate. (See Baldeschweiler, supra.) In another alternative, a grid array analogous to a dot or slot blot is used to arrange and link cDNA fragments or oligonucleotides to the surface of a substrate using a vacuum system or thermal, UV, mechanical, or chemical bonding procedures. A typical array may be produced by hand or using available materials and machines and contain grids of 8 dots, 24 dots, 96 dots, 384 dots, 1536 dots, or 6144 dots. After hybridization, the microarray is washed to remove nonhybridized probes, and a scanner is used to determine the levels and patterns of fluorescence. The scanned image is examined to determine the degree of complementarity and the relative abundance/expression level of each oligonucleotide sequence in the microarray.

VIII. Complementary Polynucleotides

Sequences complementary to the HNLP-encoding sequences, or any parts thereof, are used to detect, decrease, or inhibit expression of naturally occurring HNLP. Although use of oligonucleotides comprising from about 15 to 30 base pairs is described, essentially the same procedure is used with smaller or with larger sequence fragments. Appropriate oligonucleotides are designed using OLIGO 4.06 software and the coding sequence of HNLP. To inhibit transcription, a complementary oligonucleotide is designed from the most unique 5' sequence and used to prevent promoter binding to the coding sequence. To inhibit translation, a complementary oligonucleotide is designed to prevent ribosomal binding to the HNLP-encoding transcript.

IX. Expression of HNLP

Expression of HNLP is accomplished by subcloning the cDNAs into appropriate vectors and transforming the vectors into host cells. In this case, the cloning vector is also used to express HNLP in E. coli. This vector contains a promoter for β-galactosidase upstream of the cloning site, followed by sequence containing the amino-terminal Met and the subsequent seven residues of β-galactosidase. Immediately following these eight residues is a bacteriophage promoter useful for transcription and a linker containing a number of unique restriction sites.

Induction of an isolated, transformed bacterial strain with isopropyl beta-D-thiogalactopyranoside (IPTG) using standard methods produces a fusion protein which consists of the first 8 residues of β-galactosidase, about 5 to 15 residues of linker, and the full length protein. The signal residues direct the secretion of HNLP into bacterial growth media which can be used directly in the following assay for activity.

X. Demonstration of HNLP Activity

HNLP is assayed by measuring the ability of HNLP to bind histone H1. Nitrocellulose filters are first incubated in binding buffer (50 mM NaCl, 20 mM Tris/HCl, 1 mM EDTA, 0.2% Ficoll, 0.2% polyvinylpyrrolidone, 0.2% bovine serum albumin). Varying amounts of sample containing HNLP are deposited onto the filters. The filters are then incubated for 3 hours at 37° C. with $^{32}$P-labeled histone H1 (10 µg), in binding buffer containing 1 mg/ml lysozyme. The filters are then washed, and radioactivity is determined by scintillation counting. (Erard, M. S. et al., supra.)

XI. Production of HNLP Specific Antibodies

HNLP substantially purified using PAGE electrophoresis (Harrington, M. G. (1990) Methods Enzymol. 182:488–495), or other purification techniques, is used to immunize rabbits and to produce antibodies using standard protocols. The HNLP amino acid sequence is analyzed using DNASTAR software (DNASTAR Inc) to determine regions of high immunogenicity, and a corresponding oligopeptide is synthesized and used to raise antibodies by means known to those of skill in the art. Selection of appropriate epitopes, such as those near the C-terminus or in hydrophilic regions, is described by Ausubel F. M. et al. (1995 and periodic supplements) Current Protocols in Molecular Biology, ch. 11, John Wiley & Sons, New York, N.Y. and by others.

Typically, the oligopeptides are 15 residues in length, and are synthesized using an Applied Biosystems peptide synthesizer model 431A using fmoc-chemistry and coupled to KLH (Sigma, St. Louis, Mo.) by reaction with N-maleimidobenzoyl-N-hydroxysuccinimide ester (MBS), following the procedure described in Ausubel et al., supra. Rabbits are immunized with the oligopeptide-KLH complex in complete Freund's adjuvant. Resulting antisera are tested for antipeptide activity, for example, by binding the peptide to plastic, blocking with 1% BSA, reacting with rabbit antisera, washing, and reacting with radio-iodinated goat anti-rabbit IgG.

XII. Purification of Naturally Occurring HNLP Using Specific Antibodies

Naturally occurring or recombinant HNLP is substantially purified by immunoaffinity chromatography using antibodies specific for HNLP. An immunoaffinity column is constructed by covalently coupling HNLP antibody to an activated chromatographic resin, such as CNBr-activated SEPHAROSE (Pharmacia & Upjohn). After the coupling, the resin is blocked and washed according to the manufacturer's instructions.

Media containing HNLP are passed over the immunoaffinity column, and the column is washed under conditions that allow the preferential absorbance of HNLP (e.g., high ionic strength buffers in the presence of detergent). The column is eluted under conditions that disrupt antibody/HNLP binding (e.g., a buffer of pH 2 to pH 3, or a high concentration of a chaotrope, such as urea or thiocyanate ion), and HNLP is collected.

XIII. Identification of Molecules Which Interact with HNLP

HNLP or biologically active fragments thereof are labeled with $^{125}$I Bolton-Hunter reagent. (Bolton et al. (1973) Biochem. J. 133:529.) Candidate molecules previously arrayed in the wells of a multi-well plate are incubated with the labeled HNLP, washed, and any wells with labeled HNLP complex are assayed. Data obtained using different concentrations of HNLP are used to calculate values for the number, affinity, and association of HNLP with the candidate molecules.

Various modifications and variations of the described methods and systems of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

What is claimed is:

1. An isolated and purified polynucleotide sequence encoding the amino acid sequence of SEQ ID NO:1.

2. A composition comprising the polynucleotide sequence of claim 1.

3. An isolated and purified polynucleotide sequence which is fully complementary to the polynucleotide sequence of claim 1.

4. An isolated and purified polynucleotide sequence comprising SEQ ID NO:2.

5. An isolated and purified polynucleotide sequence which is fully complementary to the polynucleotide sequence of claim 4.

6. An expression vector containing at least a fragment of the polynucleotide sequence of claim 1.

7. A host cell containing the expression vector of claim 6.

8. A method for producing a polypeptide comprising the amino acid sequence of SEQ ID NO:1, the method comprising the steps of:

(a) culturing the host cell of claim 7 under conditions suitable for the expression of the polypeptide; and (b) recovering the polypeptide from the host cell culture.

9. A method for detecting a polynucleotide encoding the amino acid sequence of SEQ ID NO:1 in a biological sample containing nucleic acids, the method comprising the steps of:

(a) hybridizing the polynucleotide of claim 3 to at least one of the nucleic acids of the biological sample, thereby forming a hybridization complex; and (b) detecting the hybridization complex, wherein the presence of the hybridization complex correlates with the presence of a polynucleotide encoding the amino acid sequence of SEQ ID NO:1 in the biological sample.

10. The method of claim 9 wherein the nucleic acids of the biological sample are amplified by the polymerase chain reaction prior to the hybridizing step.

* * * * *

```
                          SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:
        (A) LENGTH: 545 amino acids
        (B) TYPE: amino acid
        (C) STRANDEDNESS: single
        (D) TOPOLOGY: linear (vii) IMMEDIATE SOURCE:
        (A) LIBRARY: TLYMNOT05
        (B) CLONE: 2809795

(xi) SEQUENCE DESCRIPTION: SEQ ID NO:1:

Met Ala Thr Glu His Val Asn Gly Asn Gly Thr Glu Pro Met Asp
1               5                   10                  15

Thr Thr Ser Ala Val Ile His Ser Glu Asn Phe Gln Thr Leu Leu Asp
            20                  25                  30

Ala Gly Leu Pro Gln Lys Val Ala Glu Lys Leu Asp Glu Ile Tyr Val
        35                  40                  45

Ala Gly Leu Val Ala His Ser Asp Leu Asp Glu Arg Ala Ile Glu Ala
    50                  55                  60

Leu Lys Glu Phe Asn Glu Asp Gly Ala Leu Ala Val Leu Gln Gln Phe
65                  70                  75                  80

Lys Asp Ser Asp Leu Ser His Val Gln Asn Lys Ser Ala Phe Leu Cys
                85                  90                  95

Gly Val Met Lys Thr Tyr Arg Gln Arg Glu Lys Gln Gly Thr Lys Val
            100                 105                 110

Ala Asp Ser Ser Lys Gly Pro Asp Glu Ala Lys Ile Lys Ala Leu Leu
        115                 120                 125

Glu Arg Thr Gly Tyr Thr Leu Asp Val Thr Thr Gly Gln Arg Lys Tyr
    130                 135                 140

Gly Gly Pro Pro Pro Asp Ser Val Tyr Ser Gly Gln Gln Pro Ser Val
145                 150                 155                 160
```

―continued

```
Gly Thr Glu Ile Phe Val Gly Lys Ile Pro Arg Asp Leu Phe Glu Asp
            165                 170                 175
Glu Leu Val Pro Leu Phe Glu Lys Ala Gly Pro Ile Trp Asp Leu Arg
        180                 185                 190
Leu Met Met Asp Pro Leu Thr Gly Leu Asn Arg Gly Tyr Ala Phe Val
    195                 200                 205
Thr Phe Cys Thr Lys Glu Ala Ala Gln Glu Ala Val Lys Leu Tyr Asn
210                 215                 220
Asn His Glu Ile Arg Ser Gly Lys His Ile Gly Val Cys Ile Ser Val
225                 230                 235                 240
Ala Asn Asn Arg Leu Phe Val Gly Ser Ile Pro Lys Ser Lys Thr Lys
                245                 250                 255
Glu Gln Ile Leu Glu Glu Phe Ser Lys Val Thr Glu Gly Leu Thr Asp
            260                 265                 270
Val Ile Leu Tyr His Gln Pro Asp Asp Lys Lys Asn Arg Gly Phe
        275                 280                 285
Cys Phe Leu Glu Tyr Glu Asp His Lys Thr Ala Ala Gln Ala Arg Arg
    290                 295                 300
Arg Leu Met Ser Gly Lys Val Lys Val Trp Gly Asn Val Gly Thr Val
305                 310                 315                 320
Glu Trp Ala Asp Pro Ile Glu Asp Pro Asp Pro Glu Val Met Ala Lys
                325                 330                 335
Val Lys Val Leu Phe Val Arg Asn Leu Ala Asn Thr Val Thr Glu Glu
            340                 345                 350
Ile Leu Glu Lys Ala Phe Ser Gln Phe Gly Lys Leu Glu Arg Val Lys
        355                 360                 365
Lys Leu Lys Asp Tyr Ala Phe Ile His Phe Asp Glu Arg Asp Gly Ala
    370                 375                 380
Val Lys Ala Met Glu Glu Met Asn Gly Lys Asp Leu Glu Gly Glu Asn
385                 390                 395                 400
Ile Glu Ile Val Phe Ala Lys Pro Pro Asp Gln Lys Arg Lys Glu Arg
                405                 410                 415
Lys Ala Gln Arg Gln Ala Ala Lys Asn Gln Met Tyr Asp Asp Tyr Tyr
            420                 425                 430
Tyr Tyr Gly Pro Pro His Met Pro Pro Pro Thr Arg Gly Arg Gly Arg
        435                 440                 445
Gly Gly Arg Gly Gly Tyr Gly Tyr Pro Pro Asp Tyr Tyr Gly Tyr Glu
    450                 455                 460
Asp Tyr Tyr Asp Tyr Tyr Gly Tyr Asp Tyr His Asn Tyr Arg Gly Gly
465                 470                 475                 480
Tyr Glu Asp Pro Tyr Tyr Gly Tyr Glu Asp Phe Gln Val Gly Ala Arg
                485                 490                 495
Gly Arg Gly Gly Arg Gly Ala Arg Gly Ala Ala Pro Ser Arg Gly Arg
            500                 505                 510
Gly Ala Ala Pro Pro Arg Gly Arg Ala Gly Tyr Ser Gln Arg Gly Gly
        515                 520                 525
Pro Gly Ser Ala Arg Gly Val Arg Ala Gly Lys Arg Gly Arg Gly Arg
    530                 535                 540
Ser
545
```

(2) INFORMATION FOR SEQ ID NO:2:

(i) SEQUENCE CHARACTERISTICS:
        (A) LENGTH: 2079 base pairs (B) TYPE: nucleic acid
(C) STRANDEDNESS: single
(D) TOPOLOGY: linear (vii) IMMEDIATE SOURCE:
(A) LIBRARY: TLYMNOT05
(B) CLONE: 2809795

(xi) SEQUENCE DESCRIPTION: SEQ ID NO:2:

```
GGGCGCGCGC GCGCACCGGG AGCGCGCTCG GAGGCGAGTG GAACTGGATC GGGTTTGCTG      60
CCAGCGGCGT GAGCTTCGGC CGGCATTTTA CAACAGCTCC ACTCGCGCCG GACACAGGGA     120
GCAGCGAGCA CGCGTTTCCC GCAACCCGAT ACCATCGGAC AGGATTTCTC CGCCTCAGCC     180
CAACGGGAG ATCTCTGGAA ACATGGCTAC AGAACATGTT AATGGAAATG GTACTGAAGA      240
GCCCATGGAT ACTACTTCTG CAGTTATCCA TTCAGAAAAT TTTCAGACAT TGCTTGATGC     300
TGGTTTACCA CAGAAAGTTG CTGAAAAACT AGATGAAATT TACGTTGCAG GGCTAGTTGC     360
ACATAGTGAT TTAGATGAAA GAGCTATTGA AGCTTTAAAA GAATTCAATG AAGACGGTGC     420
ATTGGCAGTT CTTCAACAGT TTAAAGACAG TGATCTCTCT CATGTTCAGA ACAAAAGTGC     480
CTTTTTATGT GGAGTCATGA AGACTTACGC AGAGAGAA AAACAAGGGA CCAAAGTAGC      540
AGATTCTAGT AAAGGACCAG ATGAGGCAAA AATTAAGGCA CTCTTGGAAA GAACAGGCTA     600
CACACTTGAT GTGACCACTG GACAGAGGAA GTATGGAGGA CCACCTCCAG ATTCCGTTTA     660
TTCAGGTCAG CAGCCTTCTG TTGGCACTGA GATATTTGTG GGAAAGATCC CAAGAGATCT     720
ATTTGAGGAT GAACTTGTTC CATTATTTGA GAAAGCTGGA CCTATATGGG ATCTTCGTCT     780
AATGATGGAT CCACTCACTG GTCTCAATAG AGGTTATGCG TTTGTCACTT TTTGTACAAA     840
AGAAGCAGCT CAGGAGGCTG TTAAACTGTA TAATAATCAT GAAATTCGTT CTGGAAAACA     900
TATTGGTGTC TGCATCTCAG TTGCCAACAA TAGGCTTTTT GTGGGCTCTA TTCCTAAGAG     960
TAAAACCAAG GAACAGATTC TTGAAGAATT TAGCAAAGTA ACAGAGGGTC TTACAGACGT    1020
CATTTTATAC CACCAACCGG ATGACAAGAA AAAAACAGA GGCTTTTGCT TCTTGAATA     1080
TGAAGATCAC AAAACAGCTG CCCAGGCAAG GCGTAGGTTA ATGAGTGGTA AAGTCAAGGT    1140
CTGGGGGAAT GTTGGAACTG TTGAATGGGC TGATCCTATA GAAGATCCTG ATCCTGAGGT    1200
TATGGCAAAG GTAAAGTGC TGTTTGTACG CAACCTTGCC AATACTGTAA CAGAAGAGAT     1260
TTTAGAAAAG GCATTTAGTC AGTTTGGGAA ACTGGAACGA GTGAAGAAGT TAAAAGATTA    1320
TGCGTTCATT CATTTTGATG AGCGAGATGG TGCTGTCAAG GCTATGGAAG AAATGAATGG    1380
CAAAGACTTG GAGGGAGAAA ATATTGAAAT TGTTTTTGCC AAGCCACCAG ATCAGAAAAG    1440
GAAAGAAAGA AAAGCTCAGA GGCAAGCAGC AAAAAATCAA ATGTATGACG ATTACTACTA    1500
TTATGGTCCA CCTCATATGC CCCCTCCAAC AAGAGGTCGA GGGCGTGGAG GTAGAGGTGG    1560
TTATGGATAT CCTCCAGATT ATTATGGATA TGAAGATTAT TATGATTATT ATGGTTATGA    1620
TTACCATAAC TATCGTGGTG GATATGAAGA TCCATACTAT GGTTATGAAG ATTTTCAAGT    1680
TGGAGCTAGA GGAAGGGGTG GTAGAGGAGC AAGGGGTGCT GCTCCATCCA GAGGTCGTGG    1740
GGCTGCTCCT CCCCGCGGTA GAGCCGGTTA TTCACAGAGA GGAGGTCCTG GATCAGCAAG    1800
AGGCGTTCGA GCAGGGAAAA GGGGTCGAGG CCGGTCCTGA CCTGTTACAA TGAAGACTGA    1860
CTTGCTATGT GGGATTACAC CAGAAGCTTG CAGTGGAGTA ATGGTAAGGA AATCAAGCAA    1920
CCTTAAATAT GTCGGCTGTA TAGGAGCATA TTCTATTGCA GAAGACCTTC CTATGAAGAT    1980
CATGGAATCA AATACGGGAC ATTGAACTAA TACTTGGACT TTGATATGAA TTTCTTTAAC    2040
AATTTTCTCT GCAGTGCAAG TTATTAAACT AAAGCTACT                            2079
```

(2) INFORMATION FOR SEQ ID NO:3:

(i) SEQUENCE CHARACTERISTICS:
        (A) LENGTH: 714 amino acids
        (B) TYPE: amino acid
        (C) STRANDEDNESS: single
        (D) TOPOLOGY: linear (vii) IMMEDIATE SOURCE:
        (A) LIBRARY: GenBank
        (B) CLONE: 128842

(xi) SEQUENCE DESCRIPTION: SEQ ID NO:3:

```
Met Val Lys Leu Ala Lys Ala Gly Lys Thr His Gly Glu Ala Lys Lys
 1               5                  10                  15

Met Ala Pro Pro Lys Glu Val Glu Glu Asp Ser Glu Asp Glu Glu
            20                  25                  30

Met Ser Glu Glu Asp Asp Ser Ser Gly Glu Glu Val Val Ile Pro
        35                  40                  45

Gln Lys Lys Gly Lys Ala Thr Ala Thr Pro Ala Lys Lys Val Val
    50                  55                  60

Val Ser Gln Thr Lys Lys Val Ala Val Pro Thr Pro Ala Lys Lys Ala
65                  70                  75                  80

Ala Val Thr Pro Gly Lys Lys Ala Ala Thr Pro Ala Lys Lys Ala
                85                  90                  95

Val Thr Pro Ala Lys Ala Val Ala Thr Pro Gly Lys Lys Gly Ala Thr
                100                 105                 110

Gln Ala Lys Ala Leu Val Ala Thr Pro Gly Lys Lys Gly Ala Val Thr
            115                 120                 125

Pro Ala Lys Gly Ala Lys Asn Gly Lys Asn Ala Lys Lys Glu Asp Ser
            130                 135                 140

Asp Glu Asp Glu Asp Asp Asp Asp Glu Asp Asp Ser Asp Glu Asp
145                 150                 155                 160

Glu Glu Asp Glu Glu Glu Asp Glu Phe Glu Pro Pro Val Val Lys Gly
                165                 170                 175

Lys Gln Gly Lys Val Ala Ala Ala Pro Ala Ser Glu Asp Glu Asp
            180                 185                 190

Glu Glu Glu Asp Glu Glu Glu Glu Asp Glu Glu Glu Asp
                195                 200                 205

Asp Ser Glu Glu Glu Glu Ala Met Glu Ile Thr Pro Ala Lys Gly Lys
            210                 215                 220

Lys Ala Pro Ala Lys Val Val Pro Val Lys Ala Lys Asn Val Ala Glu
225                 230                 235                 240

Glu Asp Asp Asp Asp Glu Glu Asp Glu Asp Glu Glu Asp Glu
                245                 250                 255

Glu Glu Glu Glu Asp Glu Glu Glu Glu Glu Glu Glu Glu Glu
                260                 265                 270

Pro Val Lys Pro Ala Pro Gly Lys Arg Lys Lys Glu Met Thr Lys Gln
            275                 280                 285

Lys Glu Val Pro Glu Ala Lys Lys Gln Lys Val Glu Gly Ser Glu Ser
    290                 295                 300

Thr Thr Pro Phe Asn Leu Phe Ile Gly Asn Leu Asn Pro Asn Lys Ser
305                 310                 315                 320

Val Ala Glu Leu Lys Val Ala Ile Ser Glu Pro Phe Ala Lys Asn Asp
                325                 330                 335

Leu Ala Val Val Asp Val Arg Thr Gly Thr Asn Arg Lys Phe Gly Tyr
                340                 345                 350
```

```
Val Asp Phe Glu Ser Ala Glu Asp Leu Glu Lys Ala Leu Glu Leu Thr
        355                 360                 365
Gly Leu Lys Val Phe Gly Asn Glu Ile Lys Leu Glu Lys Pro Lys Gly
        370                 375                 380
Arg Asp Ser Lys Lys Val Arg Ala Ala Arg Thr Leu Leu Ala Lys Asn
385                 390                 395                 400
Leu Ser Phe Asn Ile Thr Glu Asp Glu Leu Lys Glu Val Phe Glu Asp
                405                 410                 415
Ala Leu Glu Ile Arg Leu Val Ser Gln Asp Gly Lys Ser Lys Gly Ile
                420                 425                 430
Ala Tyr Ile Glu Phe Lys Ser Glu Ala Asp Ala Glu Lys Asn Leu Glu
                435                 440                 445
Glu Lys Gln Gly Ala Glu Ile Asp Gly Arg Ser Val Ser Leu Tyr Tyr
            450                 455                 460
Thr Gly Glu Lys Gly Gln Arg Gln Glu Arg Thr Gly Lys Asn Ser Thr
465                 470                 475                 480
Trp Ser Gly Glu Ser Lys Thr Leu Val Leu Ser Asn Leu Ser Tyr Ser
                485                 490                 495
Ala Thr Glu Glu Thr Leu Gln Glu Val Phe Glu Lys Ala Thr Phe Ile
                500                 505                 510
Lys Val Pro Gln Asn Gln Gln Gly Lys Ser Lys Gly Tyr Ala Phe Ile
            515                 520                 525
Glu Phe Ala Ser Phe Glu Asp Ala Lys Glu Ala Leu Asn Ser Cys Asn
            530                 535                 540
Lys Met Glu Ile Glu Gly Arg Thr Ile Arg Leu Glu Leu Gln Gly Pro
545                 550                 555                 560
Arg Gly Ser Pro Asn Ala Arg Ser Gln Pro Ser Lys Thr Leu Phe Val
                565                 570                 575
Lys Gly Leu Ser Glu Asp Thr Thr Glu Glu Thr Leu Lys Glu Ser Phe
                580                 585                 590
Glu Gly Ser Val Arg Ala Arg Ile Val Thr Asp Arg Glu Thr Gly Ser
            595                 600                 605
Ser Lys Gly Phe Gly Phe Val Asp Phe Asn Ser Glu Glu Asp Ala Lys
        610                 615                 620
Ala Ala Lys Glu Ala Met Glu Asp Gly Glu Ile Asp Gly Asn Lys Val
625                 630                 635                 640
Thr Leu Asp Trp Ala Lys Pro Lys Gly Glu Gly Gly Phe Gly Gly Arg
                645                 650                 655
Gly Gly Gly Arg Gly Gly Phe Gly Gly Arg Gly Gly Gly Arg Gly Gly
                660                 665                 670
Gly Arg Gly Gly Phe Gly Gly Arg Gly Arg Gly Gly Phe Gly Gly Arg
            675                 680                 685
Gly Gly Phe Arg Gly Gly Arg Gly Gly Gly Gly Gly Gly Gly Asp Phe
        690                 695                 700
Lys Pro Gln Gly Lys Lys Thr Lys Phe Glu
705                 710
```